(12) United States Patent
Park et al.

(10) Patent No.: US 9,468,641 B2
(45) Date of Patent: Oct. 18, 2016

(54) ANTI-INFLAMMATORY PHARMACEUTICAL COMPOSITION COMPRISING BENZOPYRANYL TETRACYCLES

(71) Applicants: SEOUL NATIONAL UNIVERSITY R&DB FOUNDATION, Seoul (KR); KYUNGPOOK NATIONAL UNIVERSITY INDUSTRY-ACADEMIC COOPERATION FOUNDATION, Daegu (KR); KYUNGPOOK NATIONAL UNIVERSITY HOSPITAL, Daegu (KR)

(72) Inventors: Seung Bum Park, Seoul (KR); Sanghee Lee, Seoul (KR); Ja Young Koo, Seoul (KR); Donghyun Lim, Gwangju (KR); Jongmin Park, Seoul (KR); Kyoungho Suk, Daegu (KR); Youngpyo Nam, Daegu (KR)

(73) Assignees: SEOUL NATIONAL UNIVERSITY R&DB FOUNDATION, Seoul (KR); KYUNGPOOK NATIONAL UNIVERSITY INDUSTRY-ACADEMIC COOPERATION FOUNDATION, Daegu (KR); KYUNGPOOK NATIONAL UNIVERSITY HOSPITAL, Daegu (KR)

( * ) Notice: Subject to any disclaimer, the term of this patent is extended or adjusted under 35 U.S.C. 154(b) by 0 days.

(21) Appl. No.: 14/688,014

(22) Filed: Apr. 16, 2015

(65) Prior Publication Data

US 2016/0038489 A1    Feb. 11, 2016

(30) Foreign Application Priority Data

Aug. 7, 2014    (KR) .................. 10-2014-0101643

(51) Int. Cl.
| | | |
|---|---|---|
| *A61K 31/5025* | (2006.01) | |
| *A61K 45/06* | (2006.01) | |
| *A61K 31/503* | (2006.01) | |

(52) U.S. Cl.
CPC ......... *A61K 31/5025* (2013.01); *A61K 31/503* (2013.01); *A61K 45/06* (2013.01)

(58) Field of Classification Search
None
See application file for complete search history.

(56) References Cited

U.S. PATENT DOCUMENTS

2009/0326015 A1*  12/2009  Park ............... C07D 491/052
                                              514/359

FOREIGN PATENT DOCUMENTS

| KR | 10-2012-0060957 A | 6/2012 |
| KR | 10-1170032 B1 | 8/2012 |

* cited by examiner

*Primary Examiner* — Michael Barker
(74) *Attorney, Agent, or Firm* — Blank Rome LLP

(57) ABSTRACT

Disclosed herein is an anti-inflammatory pharmaceutical composition comprising a benzopyranyl tetracycle compound represented by Chemical Formula 1 as an active ingredient. The compound exhibits excellent anti-inflammatory activity by perturbing the post-translational modification of the inflammation mediator HMGB, and thus finds applications in pharmaceutical compositions superior in the treatment or prevention of inflammation-related diseases.

6 Claims, 27 Drawing Sheets

ANTI-INFLAMMATORY PHARMACEUTICAL COMPOSITION COMPRISING BENZOPYRANYL TETRACYCLES

CROSS REFERENCE TO RELATED APPLICATION(S)

This application claims the benefit of Korean Patent Application No. 10-2014-0101643, filed on Aug. 7, 2014, which is hereby incorporated by reference in its entirety into this application.

BACKGROUND OF THE INVENTION

1. Technical Field

The present invention relates to an anti-inflammatory pharmaceutical composition comprising a benzopyranyl tetracycle compound.

2. Description of the Related Art

Traditional synthetic organic chemistry has been advanced with the development of target-oriented synthesis. Many organic chemists have conceived and developed various new reactions through the synthesis of diverse natural products. Since the target-oriented synthesis is configured to target and synthesize a specific natural product, the obtained compound may be represented as one of points distributed in chemical space. Thus, target oriented synthesis seems to be very limited in terms of the diversity of compound.

Many efforts have been made to track down more biologically active compounds by improving specific chemical properties of the obtained compound, resulting in the advent of combinatorial chemical synthesis.

Combinatorial chemical synthesis is a new synthetic method for the development of new materials. Whereas conventional organic synthesis methods can require a single reaction for the synthesis of one kind of compound, combinatorial chemical synthesis is efficient enough to synthesize more various and numerous compounds at the same time or to automate the multi-step synthetic process. With combinatorial chemical synthesis, it has become easier to screen biological hit and/or lead compounds of new structures and to optimize the structure and activity thereof. Combinatorial chemical synthesis has been mainly studied in medicinal chemistry, particularly greatly contributing to the study of structure-activity relationship, and also has allowed for various substitution reactions in a specific structure, ensuring skeletal diversity.

Developed as a different and new concept in organic synthesis, diversity-oriented synthesis is configured to synthesize a collection of structurally-diverse compounds distributed in the chemical space and to search for new biologically active compounds among the collection by High Throughput Screening.

In diversity-oriented synthesis, compounds having different core skeletons can be prepared at the same time, and can be constructed into a library from which various different active compounds thus can be identified by various screening methods.

Introduction of the concept of privileged structure to the diversity-oriented synthesis is very advantageous for searching biologically active compounds.

As used herein, the term "privileged structure" refers to a molecular framework found in common in many natural products or biologically active molecules. The application of the privileged structure to diversity-oriented synthesis has been attempted over a long period of time.

Inflammation is a pathological condition of an abscess caused by foreign infectious agents (bacteria, fungi, virus, various kinds of allergens, etc.). For example, when foreign bacteria invade into and proliferate in a tissue, the leukocytes of the body recognize and actively attack the proliferating foreign bacteria, during which leukocytes die and bacteria are killed by the leukocytes. The dead leukocytes and bacterial lysates accumulate in the tissue, forming an abscess. The abscess formed by inflammation can be treated through anti-inflammation activity. Anti-inflammation activity refers to a process that reduces inflammation in which the proliferation of the foreign agent, such as bacteria, is inhibited with the aid of an anti-inflammatory agent, for example, an antibacterial agent, or in which macrophages are activated to digest and excrete the foreign materials accumulated in the abscess. Inflammation refers to a biological protective response of tissues to harmful stimuli. Inflammation is a protective attempt by the organism to remove the injurious stimuli and to initiate the healing process for rehabilitating the cells or tissues on which organic lesion has been imposed by the invasion of the stimuli. Factors involved in these serial processes are local vascular tissues, various tissue cells of the body fluid, immune cells, etc. Like the inflammation that is normally induced by foreign pathogens, the defense mechanism for protecting the body is indispensible for survival. However, temporally or spatially inappropriate inflammatory responses play a great role in causing a broad spectrum of diseases including those that are believed to not be related with leukocytes, such as arthritis and Alzheimer disease, as well as those apparently induced by leukocyte components, such as autoimmune diseases, asthma, and atherosclerosis. In such inflammatory diseases, leukocytes are incited to rush to the affected tissue upon an autoimmune response where an antibody inadvertently recognizes a host protein, or by inappropriate triggers, such as accumulated tissue injury, for example, apoptotic bodies of permanent cells, extracellular cholesterol deposits, or intrapulmonary particulates. The leukocytes, although crowded, cannot dispose of all the triggers (for example, leukocytes cannot remove or kill all autoimmune antigen-expressing host cells, or cannot phagocyte too excessively large particles from the host cells). Hence, such diseases occasionally become chronic and continue to release inflammatory cytokines, dispatching additional leukocytes to unnecessary sites where chronic inflammation is thus formed. This inflammatory response is reported to induce chronic progressive diseases such as arteriosclerosis, obesity, insulin resistance, rheumatoid arthritis, glomerulonephritis, cancer, etc. and to play an important role in the progression of senescence.

With regard to the inflammatory response, HMGB has recently been proven to induce inflammation (Korean Patent No. 10-1170032). HMGB (high mobility group box protein) refers to a superfamily of the nuclear proteins that are involved in nucleosome stabilization, gene transcription, and neurite outgrowth. When acetylated or phosphorylated, HMGB proteins are translocated from the nucleus to the cytoplasm and the extracellular space. Also, they are reported to associate with the transmembrane receptors RAGE, TLRs 2 and 4, and syndecan-1 (CD138) to activate NF-κB and ERK1/2.

Leading to the present invention, intensive and thorough research into the treatment of inflammatory diseases resulted in the finding that benzopyranyl tetracycles inhibit the activity of HMGB proteins responsible for inflammation, and thus are useful as anti-inflammatory agents.

RELATED ART DOCUMENT

Patent Document (Patent Document 1) Korean Patent No. 10-1170032

SUMMARY OF THE INVENTION

It is therefore an object of the present invention to provide a pharmaceutical composition having a superior anti-inflammatory effect, inhibitory of HMGB proteins, and a method of treating inflammation-related disease comprising the administration of a therapeutically effective amount of the pharmaceutical composition.

To accomplish the above object, the present invention provides an anti-inflammatory pharmaceutical composition comprising a compound represented by the following Chemical Formula 1 as an active ingredient:

[Chemical Formula 1]

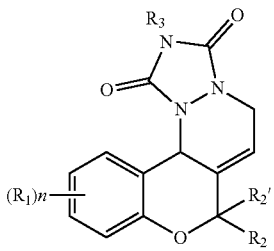

wherein, n of $(R_1)n$ is an integer of 1 to 4, with the proviso that when n is 2 or greater, $R_1$, which is identical or different, each is independently a hydrogen atom; hydroxy; halogen; C1~C6 linear or branched alkyl; C3~C10 cycloalkyl; C1~C6 linear or branched alkoxy; C2~C20 heterocycloalkyl containing N, O or S as a heteroatom; phenyl, unsubstituted or substituted with at least one selected from the group consisting of a halogen atom, amino, nitryl, nitro, C1~C30 alkyl, C2~C30 alkenyl, C1~C30 alkoxy, C3~C30 cycloalkyl, C3~C30 heterocycloalkyl containing N, O or S as a heteroatom, C6~C30 aryl, and C5~C30 heteroaryl containing N, O or S as a heteroatom; benzyl, unsubstituted or substituted with at least one selected from the group consisting of a halogen atom, amino, nitryl, nitro, C1~C30 alkyl, C2~C30 alkenyl, C1~C30 alkoxy, C3~C30 cycloalkyl, C3~C30 heterocycloalkyl containing N, O or S as a heteroatom, C6~C30 aryl, and C5~C30 heteroaryl containing N, O or S as a heteroatom; benzoyl; C1~C30 alkyl amino; C2~C30 dialkyl amino; or C1~C30 alkoxy, $R_2$ and R2', which may be identical or different, are each a hydrogen atom; hydroxy; halogen; C1~C6 linear or branched alkyl; C3~C10 cycloalkyl; C1~C6 linear or branched alkoxy; C2~C20 heterocycloalkyl containing N, O or S as a heteroatom; phenyl, unsubstituted or substituted with at least one selected from the group consisting of a halogen atom, amino, nitryl, nitro, C1~C30 alkyl, C2~C30 alkenyl, C1~C30 alkoxy, C3~C30 cycloalkyl, C3~C30 heterocycloalkyl containing N, O or S as a heteroatom, C6~C30 aryl, and C5~C30 heteroaryl containing N, O or S as a heteroatom; N-acetyl-4'-piperidyl; N-propyl-4'-piperidyl; or —$(CH_2)_m$X wherein m is an integer of 0 to 20, X is C2~C30 alkylester, C1~C30 alkylamide, C2~C30 alkylether, or carboxylic acid; or R2 and R2' may form a ring, together, $R_3$ is a hydrogen atom; C1~C6 linear or branched alkyl; C3~C10 cycloalkyl; C1~C6 linear or branched alkoxy; phenyl, unsubstituted or substituted with at least one selected from the group consisting of a halogen atom, amino, nitryl, nitro, C1~C30 alkyl, C2~C30 alkenyl, C1~C30 alkoxy, C3~C30 cycloalkyl, C3~C30 heterocycloalkyl containing N, O or S as a heteroatom, C6~C30 aryl, and C5~C30 heteroaryl containing N, O or S as a heteroatom; C2~C20 heterocycloalkyl containing N, O or S as a heteroatom; benzyl, unsubstituted or substituted with at least one selected from the group consisting of a halogen atom, amino, nitryl, nitro, C1~C30 alkyl, C2~C30 alkenyl, C1~C30 alkoxy, C3~C30 cycloalkyl, C3~C30 heterocycloalkyl containing N, O or S as a heteroatom, C6~C30 aryl, and C5~C30 heteroaryl containing N, O or S as a heteroatom; p-methylphenyl, m-methylphenyl, o-methylphenyl; p-tert-butylethylphenyl, m-tert-butylethylphenyl, or o-tert-butylethylphenyl; p-methoxyphenyl, m-methoxyphenyl, or o-methoxyphenyl; p-fluorophenyl, m-fluorophenyl, or o-fluorophenyl; p-iodophenyl, m-iodophenyl, or o-iodophenyl; p-nitrophenyl, m-nitrophenyl, or o-nitrophenyl; p-chlorophenyl; m-chlorophenyl, or o-chlorophenyl; or p-bromophenyl, m-bromophenyl, or o-bromophenyl.

In one exemplary embodiment of the present invention, $R_1$ is a hydrogen atom or hydroxy; $R_2$ and $R_2$', which may be identical or different, are each independently methyl or cyclophetyl; and $R_3$ is phenyl or p-methylphenyl.

In another exemplary embodiment of the present invention, the pharmaceutical composition may comprise at least one compound selected from the group consisting of compounds represented by the following Chemical Formulas 2 to 51 as an active ingredient.

[Chemical Formula 2]

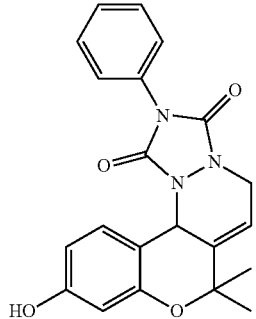

[Chemical Formula 3]

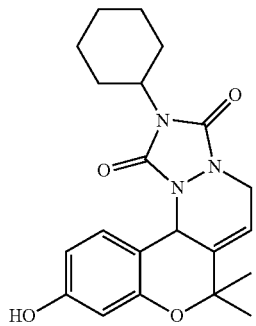

[Chemical Formula 4]
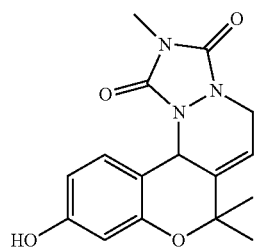
[Chemical Formula 5]
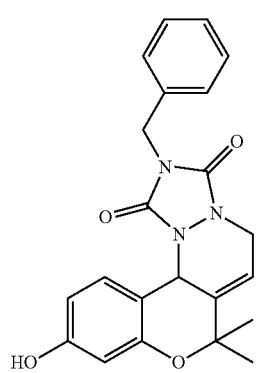
[Chemical Formula 6]
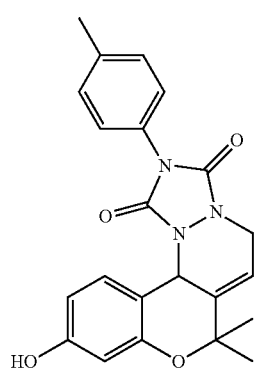
[Chemical Formula 7]
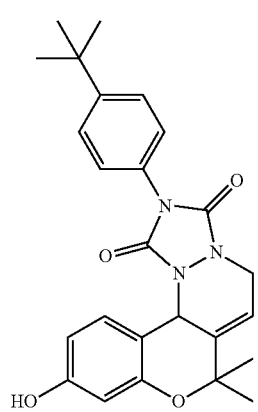
[Chemical Formula 8]
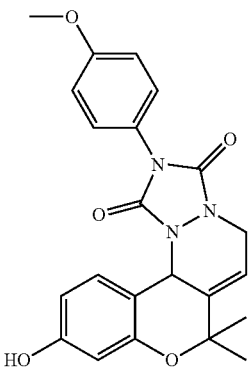
[Chemical Formula 9]
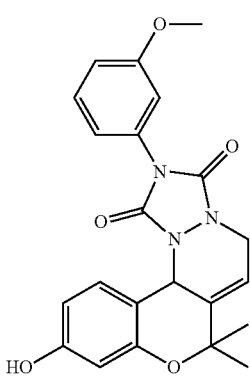
[Chemical Formula 10]
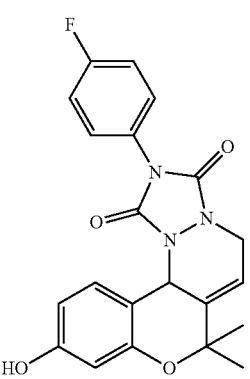
[Chemical Formula 11]
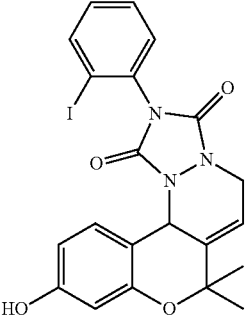

[Chemical Formula 12]
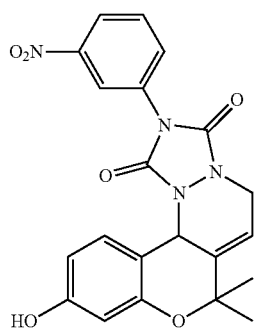
[Chemical Formula 13]
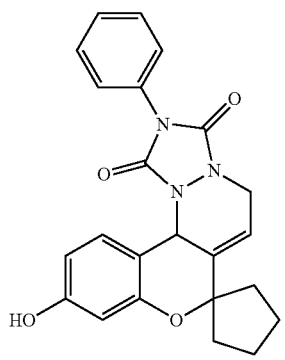
[Chemical Formula 14]
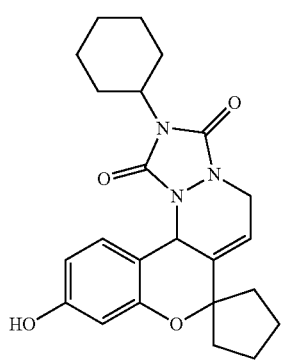
[Chemical Formula 15]
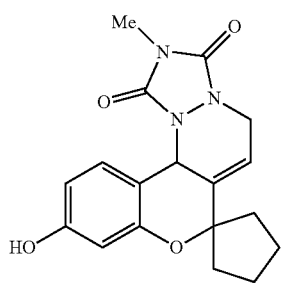
[Chemical Formula 16]
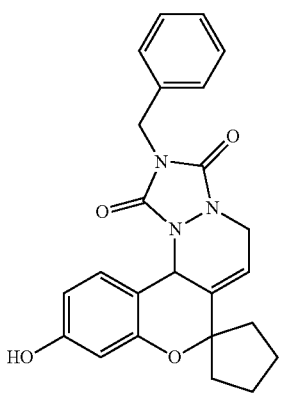
[Chemical Formula 17]
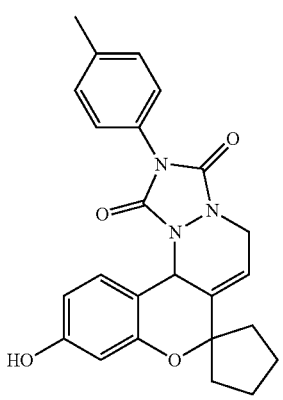
[Chemical Formula 18]
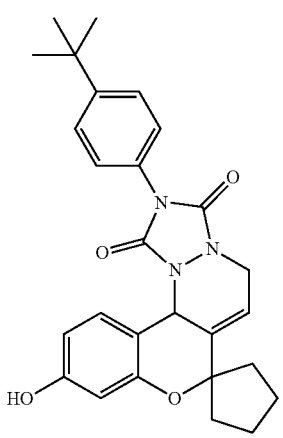

[Chemical Formula 19]
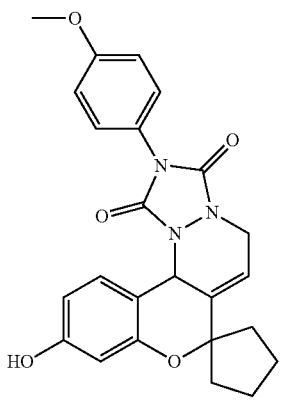
[Chemical Formula 20]
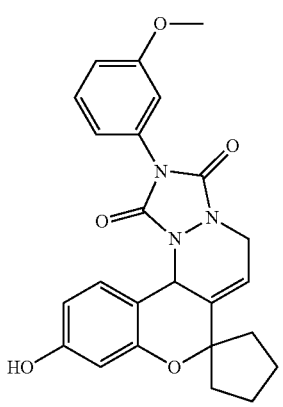
[Chemical Formula 21]
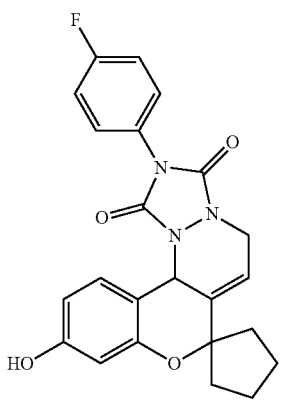
[Chemical Formula 22]
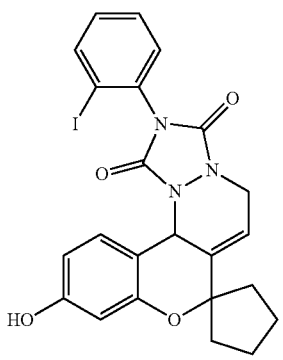
[Chemical Formula 23]
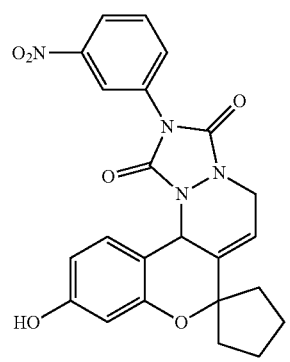
[Chemical Formula 24]
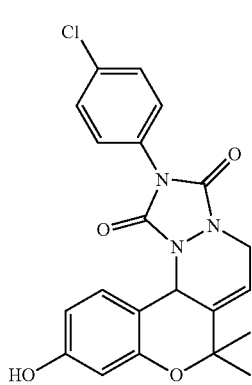
[Chemical Formula 25]
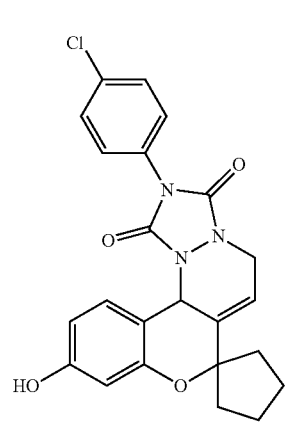
[Chemical Formula 26]
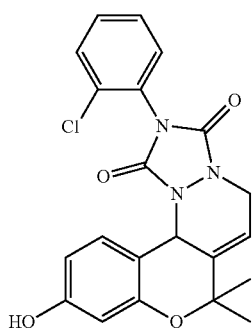

[Chemical Formula 27]
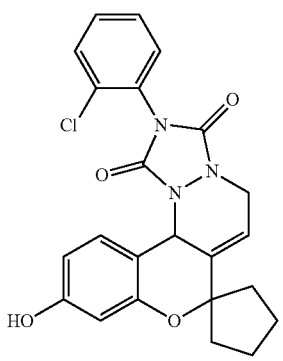
[Chemical Formula 28]
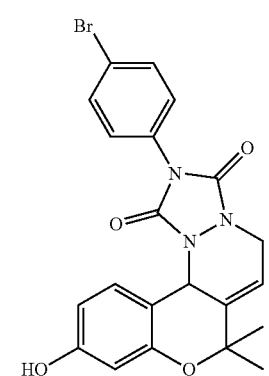
[Chemical Formula 29]
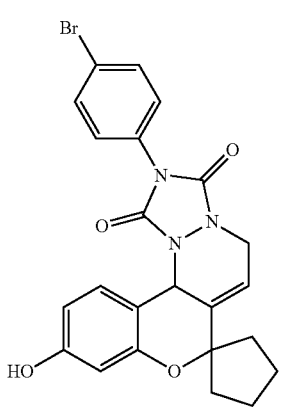
[Chemical Formula 30]
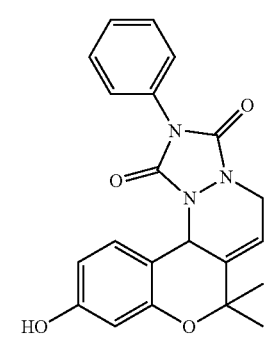
[Chemical Formula 31]
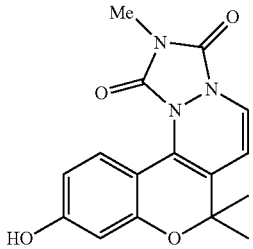
[Chemical Formula 32]
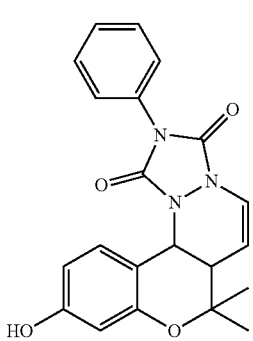
[Chemical Formula 33]
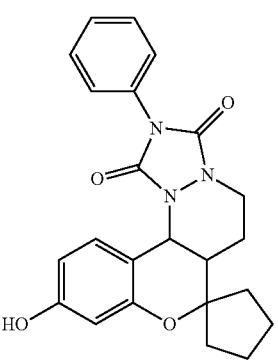
[Chemical Formula 34]
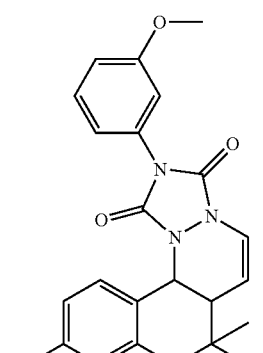
[Chemical Formula 35]
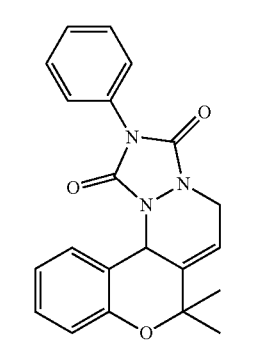

-continued
[Chemical Formula 36]
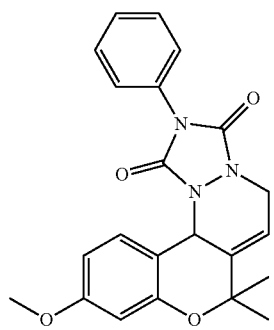
[Chemical Formula 37]
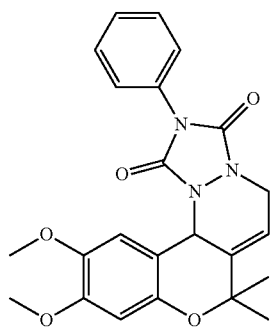
[Chemical Formula 38]
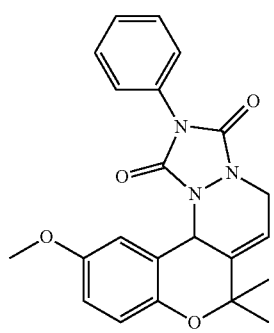
[Chemical Formula 39]
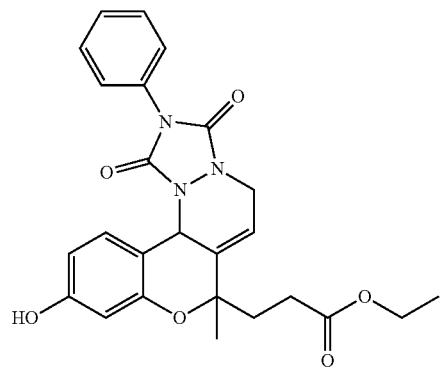
-continued
[Chemical Formula 40]
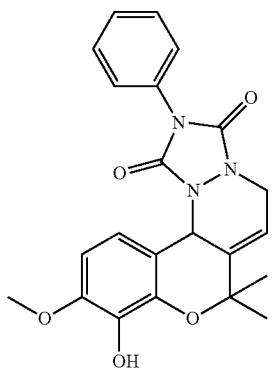
[Chemical Formula 41]
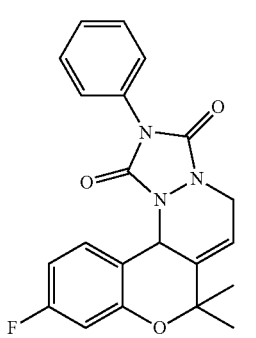
[Chemical Formula 42]
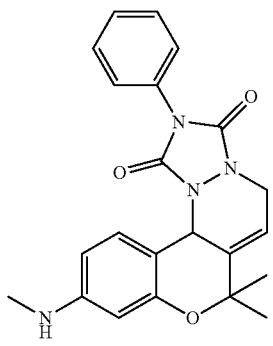
[Chemical Formula 43]
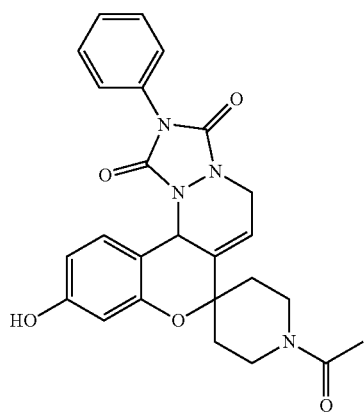

[Chemical Formula 44]
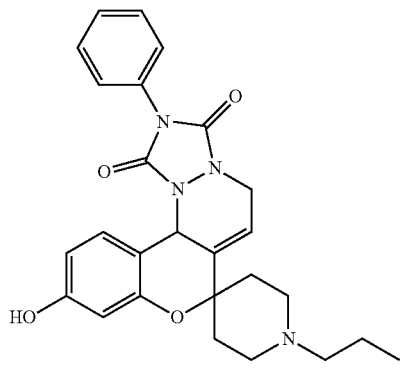
[Chemical Formula 45]
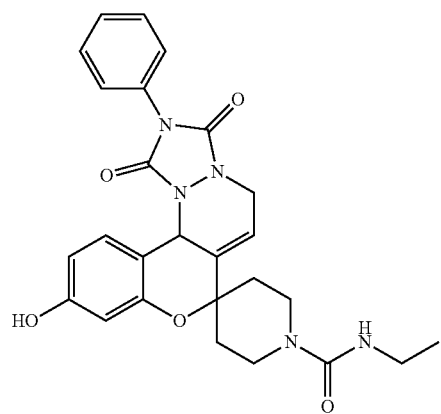
[Chemical Formula 46]
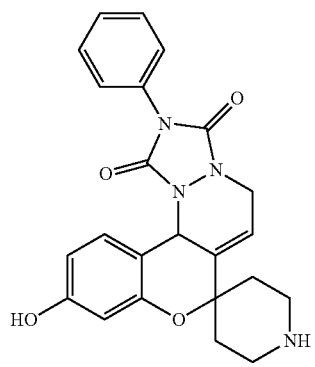
[Chemical Formula 47]
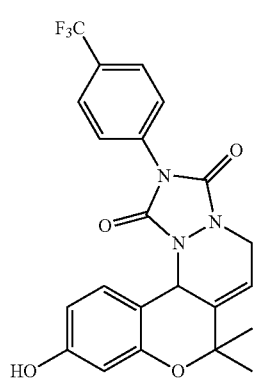
[Chemical Formula 48]
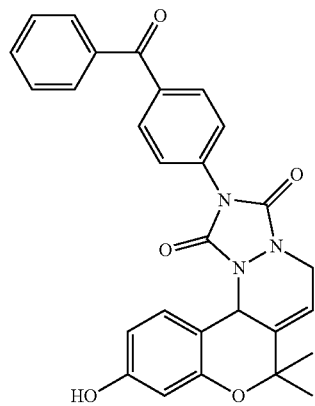
[Chemical Formula 49]
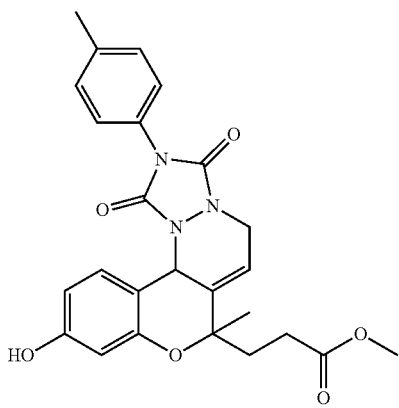
[Chemical Formula 50]
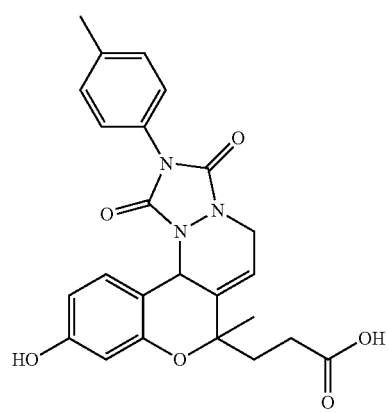

[Chemical Formula 51]

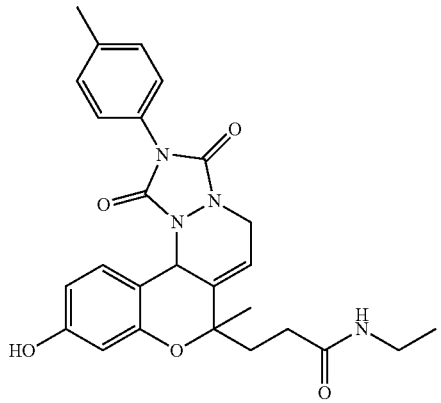

In another exemplary embodiment of the present invention, the pharmaceutical composition is of anti-inflammatory activity against at least one inflammation-related disease selected from the group consisting of gastritis, colitis, rheumatoid arthritis, nephritis, hepatitis, pancreatitis, sepsis, seizure, multiple sclerosis, Alzheimer's disease, Parkinson's disease, Huntington's disease, amyotrophic lateral sclerosis (Lou Gehrig's disease), stroke, trauma, spinal cord injury, and cancer.

In another exemplary embodiment of the present invention, the pharmaceutical composition may exhibit anti-inflammatory activity by perturbing the post-translational modification of HMGB proteins.

In another exemplary embodiment of the present invention, the pharmaceutical composition may further comprise a pharmaceutically acceptable drug, carrier or excipient.

BRIEF DESCRIPTION OF THE DRAWINGS

The above and other objects, features and advantages of the present invention will be more clearly understood from the following detailed description taken in conjunction with the accompanying drawings, in which.

DESCRIPTION OF THE PREFERRED EMBODIMENTS

Figure 1:
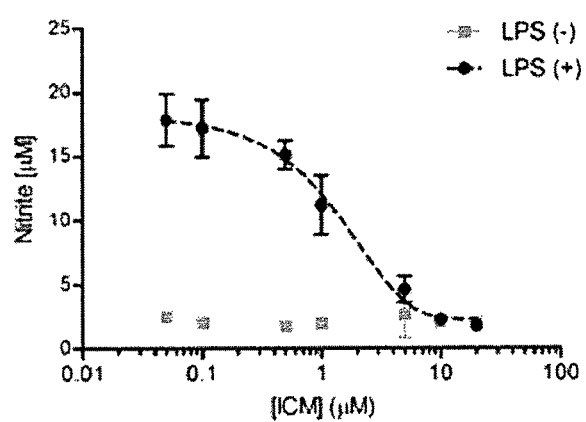
FIG. 1 shows the levels (μM) of nitrite released by BV-2 cells treated with various amounts (μM, dose-dependent) of ICM in the presence or absence of LPS.

In accordance with an aspect thereof, the present invention addresses an anti-inflammatory pharmaceutical composition comprising a compound represented by Chemical Formula 1 as an active ingredient.

Leading to the present invention, intensive and thorough research into identifying new therapeutic targets as well as new therapeutic agents to treat neuroinflammatory diseases, resulted in the finding that benzopyranyl tetracycle compounds suppress microglial-mediated inflammation as they are observed to inhibit HMGB by perturbing the post-translational modification of HMGB, as analyzed by FITGE (fluorescence difference in two-dimensional gel electrophoresis).

Below, a detailed description will be given of the present invention.

The present invention provides an anti-inflammatory pharmaceutical composition comprising a compound represented by the following Chemical Formula 1 as an active ingredient.

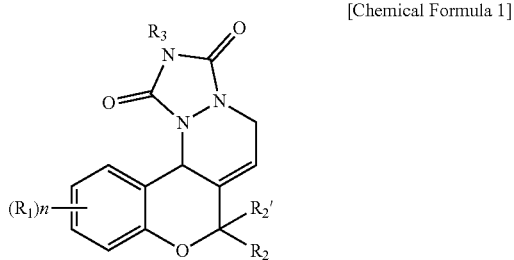

[Chemical Formula 1]

wherein, n of (R1)n is an integer of 1 to 4, with the proviso that when n is 2 or greater, R1, which is identical or different, each is independently a hydrogen atom; hydroxy; halogen; C1~C6 linear or branched alkyl; C3~C10 cycloalkyl; C1~C6 linear or branched alkoxy; C2~C20 heterocycloalkyl containing N, O or S as a heteroatom; phenyl, unsubstituted or substituted with at least one selected from the group consisting of a halogen atom, amino, nitryl, nitro, C1~C30 alkyl, C2~C30 alkenyl, C1~C30 alkoxy, C3~C30 cycloalkyl, C3~C30 heterocycloalkyl containing N, O or S as a heteroatom, C6~C30 aryl, and C5~C30 heteroaryl containing N, O or S as a heteroatom; benzyl, unsubstituted or substituted with at least one selected from the group consisting of a halogen atom, amino, nitryl, nitro, C1~C30 alkyl, C2~C30 alkenyl, C1~C30 alkoxy, C3~C30 cycloalkyl, C3~C30 heterocycloalkyl containing N, O or S as a heteroatom, C6~C30 aryl, and C5~C30 heteroaryl containing N, O or S as a heteroatom; benzoyl; C1~C30 alkyl amino; C2~C30 dialkyl amino; or C1~C30 alkoxy, R2 and R2', which may be identical or different, are each a hydrogen atom; hydroxy; halogen; C1~C6 linear or branched alkyl; C3~C10 cycloalkyl; C1~C6 linear or branched alkoxy; C2~C20 heterocycloalkyl containing N, O or S as a heteroatom; phenyl, unsubstituted or substituted with at least one selected from the group consisting of a halogen atom, amino, nitryl, nitro, C1~C30 alkyl, C2~C30 alkenyl, C1~C30 alkoxy, C3~C30 cycloalkyl, C3~C30 heterocycloalkyl containing N, O or S as a heteroatom, C6~C30 aryl, and C5~C30 heteroaryl containing N, O or S as a heteroatom; N-acetyl-4'-piperidyl; N-propyl-4'-piperidyl; or —(CH2)mX wherein m is an integer of 0 to 20, X is C2~C30 alkylester, C1~C30 alkylamide, C2~C30 alkylether, or carboxylic acid; or R2 and R2' may form a ring, together, R3 is a hydrogen atom; C1~C6 linear or branched alkyl; C3~C10 cycloalkyl; C1~C6 linear or branched alkoxy; phenyl, unsubstituted or substituted with at least one selected from the group consisting of a halogen atom, amino, nitryl, nitro, C1~C30 alkyl, C2~C30 alkenyl, C1~C30 alkoxy, C3~C30 cycloalkyl, C3~C30 heterocycloalkyl containing N, O or S as a heteroatom, C6~C30 aryl, and C5~C30 heteroaryl containing N, O or S as a heteroatom; C2~C20 heterocycloalkyl containing N, O or S as a heteroatom; benzyl, unsubstituted or substituted with at least one selected from the group consisting of a halogen atom, amino, nitryl, nitro, C1~C30 alkyl, C2~C30 alkenyl, C1~C30 alkoxy, C3~C30 cycloalkyl, C3~C30 heterocycloalkyl containing N, O or S as a heteroatom, C6~C30 aryl, and C5'~C30 heteroaryl containing N, O or S as a heteroatom; p-methylphenyl, m-methylphenyl, o-methylphenyl; p-tert-butylethylphenyl, m-tert-butylethylphenyl, or o-tert-butylethylphenyl; p-methoxyphenyl, m-methoxyphenyl, or o-methoxyphenyl; p-fluorophenyl, m-fluorophenyl, or o-fluorophenyl; p-iodophenyl, m-iodophenyl, or o-iodophenyl; p-nitrophenyl, m-nitrophenyl, or o-nitrophenyl; p-chlorophenyl; m-chlorophenyl, or o-chlorophenyl; or p-bromophenyl, m-bromophenyl, or o-bromophenyl.

In one exemplary embodiment of the present invention, R1 is a hydrogen atom or hydroxy; R2 and R2', which may be identical or different, are each independently methyl or cyclophetyl; and R3 is phenyl or p-methylphenyl.

More preferably, the compound of Chemical Formula 1 may be the compound represented by the following Chemical Formula 2.

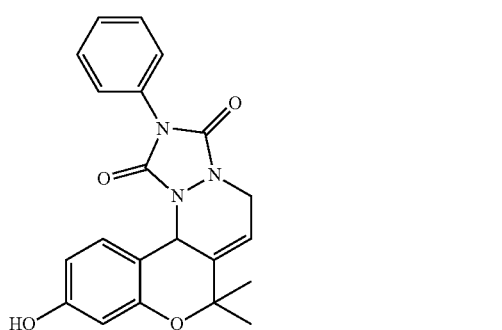

[Chemical Formula 2]

Characterized by inhibitory activity against HMGB proteins that play crucial roles in inflammation, the composition of the present invention exerts an anti-inflammatory effect. In detail, its anti-inflammatory activity results from perturbing the post-translational modification of HMGB proteins. Because the post-translational modification is responsible for controlling the cellular motility of HMGB, the composition inhibits phosphorylation or acetylation on the inflammation mediator HMGM to suppress the relocalization of HMGB, that is, translocalization from the nucleus and the cytoplasm, thereby blocking the extracellular release of HMGB.

HMGB is an inflammation mediator, which activates inflammatory singling through interaction with surface receptors. In detail, HMGB binds transmembrane receptors including RAGE, TLRs 2 and 4, and syndecan-1 (CD138) to activate the NF-κB and ERK1/2 signaling pathway. Blockage of the relocalization of HMGB, therefore, can lead to effective suppression of inflammatory responses.

Inflammation is a protective attempt by the organism to remove the injurious stimuli and to initiate the healing process for rehabilitating the cells or tissues on which an organic lesion has been imposed by the invasion of the stimuli. Factors involved in these serial processes are local vascular tissues, various tissue cells of the body fluid, immune cells, etc. Like the inflammation that is normally induced by foreign pathogens, the defense mechanism for protecting the body is indispensible for survival. However, if induced, excessively abnormal inflammation causes a broad spectrum of diseases including chronic diseases, such as gastritis, colitis, rheumatoid arthritis, nephritis, hepatitis, pancreatitis, sepsis, seizure, cancer, multiple sclerosis, Alzheimer's disease, Parkinson's disease, and Huntington's disease, and neuroinflammatory diseases, such as brain injury in an acute stage including stroke, trauma, etc. Inter alia, sepsis, seizure and cancer are affected by HMGB.

Hence, the pharmaceutical composition can be used for the treatment of at least one inflammation-related disease selected from the group consisting of gastritis, colitis, rheumatoid arthritis, nephritis, hepatitis, pancreatitis, sepsis, seizure, multiple sclerosis, Alzheimer's disease, Parkinson's disease, Huntington's disease, amyotrophic lateral sclerosis (Lou Gehrig's disease), stroke, trauma, spinal cord injury, and cancer.

The content of the compound of Chemical Formula 1 as an active ingredient in the composition of the present invention may be appropriately adjusted depending on the dosage form and purpose, the condition of the patient, the severity of disease, and the kind and progress of disease, and may range from 0.001 to 99.9% by weight, preferably from 0.1 to 99% by weight, and more preferably from 1 to 50% by weight based on the total weight of the composition, but without limitation thereto.

The dose of the pharmaceutical composition according to the present invention may be determined in consideration of various factors including the route of administration, the patient's age, sex, and condition, the severity of disease, the absorption and inactivation rate and of the active ingredient, and concomitant drugs. The active ingredient may be administered at a dose of 0.1 mg/kg (body weight) to 500 mg/kg (body weight), at a dose of 0.1 mg/kg (body weight) to 400 mg/kg (body weight) or at a dose of 1 mg/kg (body weight) to 300 mg/kg (body weight). It may be administered in a single dose or it may be spread out over multiple doses per day.

There are various routes via which the pharmaceutical composition of the present invention is introduced into mammals including humans. Administration may be achieved in any modality that is typically used in the art. For example, the pharmaceutical composition of the present invention may be administered via an oral or rectal route or by intravenous, intramuscular, subcutaneous, intrauterine epidural, or intracerebroventricular injection. The pharmaceutical composition of the present invention may be formulated into oral dosage forms such as powders, granules, tablets, capsules, suspensions, emulsions, syrups, aerosols, etc. or non-oral dosage forms such as epidermal agents, suppositories, sterile injections, etc.

The pharmaceutical composition of the present invention may further comprise a pharmaceutically suitable and physiologically additive, such as a vehicle, an excipient, a diluent, etc., in addition to the active ingredient. Examples of vehicles, excipients and diluents that are available for the pharmaceutical composition of the present invention include lactose, dextrose, sucrose, sorbitol, mannitol, xylitol, erythritol, maltitol, starch, acacia gum, alginate, gelatin, calcium phosphate, calcium silicate, cellulose, methyl cellulose, microcrystalline cellulose, polyvinyl pyrrolidone, water, methyl hydroxybenzoate, propyl hydroxybenzoate, talc, magnesium stearate, and mineral oil. In this context, the pharmaceutical composition of the present invention may be formulated in combination with a diluent or excipient such as a filler, a thickener, a binder, a humectant, a disintegrant, a surfactant, etc. Solid preparations intended for oral administration may be in the form of tablets, pills, powders, granules, capsules, and the like. In regards to these solid agents, the active ingredient of the present invention is formulated in combination with at least one excipient such as starch, calcium carbonate, sucrose, lactose, or gelatin. In addition to a simple excipient, a lubricant such as magnesium stearate, talc, etc. may be used. Among liquid preparations intended for oral administration are suspensions, internal use solutions, emulsion, syrups, and the like. Plus a simple diluent such as water or liquid paraffin, various excipients, such as humectants, sweeteners, aromatics, preservatives, and the like may be contained in the liquid preparations. Also, the pharmaceutical composition of the present invention may be in a parenteral dosage form such as sterile aqueous solutions, non-aqueous solvents, suspensions, emulsions, lyophilizates, suppositories, epidermal agents, and the like. Injectable propylene glycol, polyethylene glycol, vegetable oils such as olive oil, and esters such as ethyl oleate may be suitable for the non-aqueous solvents and suspensions. The basic materials of suppositories include Witepsol, macrogol, Tween 61, cacao butter, laurin butter, and glycerogelatin.

A better understanding of the present invention may be obtained through the following examples which are set forth to illustrate, but are not to be construed as limiting the present invention.

REFERENCE EXAMPLES

1. Cell Cultures and Animals

The following cell lines were purchased from the Korean Cell Line Bank and maintained in the condition:
BV-2 cell line: DMEM (1% A.A. 5% FBS)
HAPI cell line: DMEM (1% A.A. 5% FBS)
RAW 264.7 cell line: RPMI (1% A.A. 10% FBS)
B35-eGFP neuroblastoma cell line: constructed by stably transfecting an eGFP construct into the B35 rat neuroblastoma cells.

Primary microglia cells and astrocytes: MGCs (mixed glial cells) from the whole brains of mice at an age of 3 days were cultured. Culture media were changed initially after five days and then changed every three days. After 14 days in culture, primary astrocytes and microglia were obtained using shaking or a mild trypsinization method from mixed glial cells and maintained in DMEM (1% penicillin-streptomycin 5% FBS).

C57BL/6 mice (25-30 g) were supplied by Samtaco. The animals were maintained in temperature- and humidity-controlled conditions with a 12-h light/12-h dark cycle.

2. Griess Assay

Cells increase the secretion of nitrite when induced to be inflammatory, but decrease the secretion of nitrite in the presence of an anti-inflammatory agent. Hence, the Griess assay was used for quantification of the secretion of nitrite so as to examine the anti-inflammatory activity of the compounds. Cells were treated with the compounds in the absence or presence of 100 ng/mL LPS (lipopolysaccharide). After 24 hrs of incubation, the cell culture media were reacted with Griess reagent (0.1% naphthylethylenediamine dihydrochloride and 1% sulfanilamide in 2% phosphoric acid). Absorbance was measured at 550 nm using a microplate reader, and the level of nitrite was estimated by comparison with a sodium nitrite standard curve.

3. Cell Viability Assay

Cell viability was measured with MTT (3-(4,5-dimethyl-thiazol-2-yl)-2,5-diphenyltetrazolium bromide) or WST (water-soluble tetrazolium salt) assay kits.

4. RT-PCR

For the analysis of gene expression, cells were incubated with ICM for 6 hrs in the presence of LPS (for control, cells were treated with DMSO in the absence of LPS). Total RNA was extracted from cells using TRIzol reagent. Reverse transcription was conducted using Superscript II (Invitrogen) and oligo (dT) primers. PCR amplification was conducted using a DNA Engine Tetrad Peltier Thermal Cycler (Bio-Rad) using specific primer sets (at an annealing temperature of 55-60° C. for 20-30 cycles). To analyze PCR products, each sample was electrophoresed on a 1% agarose gel. The Gapdh (Glyceraldehyde-3-phosphate dehydrogenase) gene was used as an internal control.

5. ELISA

TNF-α secretion was measured using a TNF-α ELISA kit. Cells were treated with LPS in the absence or presence of ICM. After 24 hrs of incubation, the levels of TNF-α in the culture medium were measured with rat monoclonal anti-mouse TNF-α antibody as a capture antibody, and goat biotinylated polyclonal anti-mouse TNF-α antibody as a detection antibody. The biotinylated anti-TNF-α antibody was detected by sequential incubation with streptavidin-horseradish peroxidase conjugate. After incubation with a TMB substrate for 20 min, the color development was stopped by adding 2 N $H_2SO_4$. The absorbance was then read (450 nm and 540 nm) using a microplate reader.

6. Immunofluorescence Staining

Cells were pretreated with ICM and LPS for 1 hr and then fixed with 4% paraformaldehyde for 30 min at 20° C. and with cold methanol for 10 min at −20° C. After permeabilization with 0.3% Triton X-100 and PBS for 10 min, the fixed cells were blocked with 1% normal horse serum for 1 hr and incubated with mouse anti-p65 antibody at 4° C. for 12~16 hrs. After washing with PBS containing 0.05% Tween-20 (PBST), Alexa Fluor-488-labeled goat anti-mouse IgG antibody was added to the sample, incubated for 1 hr at room temperature and washed with PBST. Nuclei were visualized by DAPI staining. Samples were analyzed by fluorescence microscopy.

7. Microglia and Neuroblastoma Co-Culture

For the coculture of microglial cells and neuroblastoma cells, HAPI microglial cells were exposed to ICM and LPS (100 ng/ml) for 8 hrs. The medium was replaced with fresh medium containing B35-eGFP neuroblastoma cells. After 24 hrs of incubation, the viability of the B35-eGFP neuroblastoma cells was analyzed by fluorescence micrography.

8. In-Gel Analysis

Cells were treated with the compounds (ICM-BP alone or ICM-BP/ICM in combination) for 30 min and then with LPS for 2 hrs. Afterwards, the cells were irradiated with 365-nm UV light for 30 min, washed with PBS and stored at −78° C. They were lysed in RIPA buffer containing a protease inhibitor cocktail, and the protein concentration was adjusted to approximately 1 mg/ml. The proteome was labeled with Cy5-azide (40 μM), TBTA (100 μM), $CuSO_4$ (1 mM), TCEP (1 mM) and t-BuOH (5%) for 1 hrs. The mixture was treated with acetone at −20° C. for 20 mM to precipitate proteins. After centrifugation at 4° C. and 14,000 rpm for 10 mM, the pellet was washed twice with cold acetone. For 1-D gel analysis, the pellet was dissolved in Laemmli sample buffer and analyzed by electrophoresis. For 2-D gel analysis, the pellet was dissolved in rehydration buffer. The proteome labeled with ICM-BP (test group) and the control (labeled with ICM-BP/ICM) were mixed (1:1 ratio). The mixed proteomes were analyzed by 2-D gel electrophoresis. In-gel fluorescence was scanned with a Typhoon Trio (GE Healthcare).

9. Pull-Down Assay

Cell lysates were prepared according to the same protocol used for the in-gel analysis (lyzed in RIPA buffer containing a protease inhibitor cocktail). The proteome was reacted with 40 μM biotin-azide, 100 μM TBA, 1 mM $CuSO_4$, 1 mM TCEP, and 5% t-BuOH for 1 hr, followed by precipitation at −20° C. for 20 mM with acetone. After centrifugation at 4° C. and 14,000 rpm for 10 min, the pellet was washed twice with cold acetone. The pellets were dissolved in PBS containing 1.2% SDS and then diluted with PBS containing 0.2% SDS. The samples were incubated with avidin beads for 2 hrs at room temperature and washed several times with PBS. Samples were boiled with Laemmli sample buffer, and analyzed by electrophoresis and immunoblotting for HMGB2.

10. Western Blot Analysis

The proteomes were analyzed by electrophoresis, and then transferred to PVDF membranes. The membranes were blocked with 2% BSA in TBST for 1 hr or longer. The membranes were incubated overnight at 4° C. with a primary antibody, and then washed with TBST. The resulting membranes were incubated with an HRP-conjugated secondary antibody for 1 hr at room temperature. After washing, the membranes were developed using an enhanced chemiluminescence (ECL) detection kit, and the chemiluminescent signal was detected by an imaging system.

11. SPR (Surface Plasmon Resonance) Assay

To determine the dissociation constant of the interaction of ICM with HMGB, SPR analysis was performed using Biacore T100. A carboxyl group bound onto a CM5 chip of the biosensor was activated with EDC(1-ethyl-3-(3-dimethylaminopropyl)-carbodiimide) and NHS(N-hydroxysuccinimide) to form reactive succinimide ester. HMGB1 (10 mM Na-acetate, pH 4.0) and HMGB2 (10 mM Na-acetate, pH 4.5) proteins were immobilized via an amide bond onto the sensor chip, followed by quenching excess succinimide ester with 1 M ethanolamine-HCl (pH 8.0). PBS was used as a running buffer for the immobilization. After immobilization, various concentrations of ICM were injected (for 60 sec at a flow rate of 30 µl/min). Dissociation was observed at the same flow rate for 300 sec. For this, a buffer containing 10-mM HEPES (pH 7.4), 5% DMSO, 150 mM NaCl, 3 mM EDTA, and 0.005% P20 was injected. Binding was measured at 25° C. The measurements were analyzed using Biacore T100 Evaluation software (GE Healthcare). Finally, the curve was obtained by normalizing to the control. The dissociation constant was calculated by fitting the curve to the 1:1 binding model.

12. siRNA-Mediated Knockdown Assay

The siRNA transfection of BV-2 microglial cells was performed using Lipofectamine™ 2000 (Invitrogen). Forty-eight hours after transfection, the cells were used for further experiments.

13. Subcellular Fractionation and Secretion Analysis

After exposure to ICM in the presence of LPS for 18 hrs, cells were lysed in subcellular fraction buffer (250 mM sucrose, 20 mM HEPES, 10 mM KCl, 1 mM EDTA, 1 mM EGTA, 1 mM DTT, and protease inhibitor cocktail), passed through a 25-Ga needle several times, and incubated on ice for 20 min. After centrifugation at 3,000 rpm for 5 min, the pellet and the supernatant were separated. The nuclear pellet was washed and then resuspended in standard lysis buffer with 10% glycerol and 0.1% SDS. The cytosolic fraction was obtained by centrifugation of the separated supernatant at 8,000 rpm for 15 min. The conditioned medium was collected for the analysis of the extracellular level of HMGBs and concentrated with Amicon Ultra 10K filters. The samples were analyzed by electrophoresis and western blotting.

14. Immunoprecipitation Analysis

For the analysis of post-translational modification levels on HMGB, immunoprecipitation was performed. After a 4-hour incubation with a compound in the presence of LPS, cells were harvested and lysed in IP buffer containing a protease inhibitor cocktail and an appropriate inhibitor (PMSF, NaF and $Na_3VO_4$ for phosphorylation or nicotinamide and trichostatin A for acetylation). The concentration of protein was measured by BCA assay, and the lysates were incubated overnight with an anti-phosphoserine antibody or an anti-acetylated lysine antibody at 4° C., followed by precipitation with a protein G immunoprecipitation kit (Sigma). Each of the samples was analyzed for HMGB2 level by western blot assays.

15. LPS Neuroinflammation Model

All experiments were performed on 11-week-old male C57BL/6 mice. The animals were divided into four experimental groups (group 1: control treated with vehicle; group 2: treated with ICM; group 3: treated with LPS and vehicle; and group 4: treated with LPS and ICM). ICM (2 or 10 mg per kg body weight) or vehicle (distilled water containing 5% DMSO and 40% polyethylene glycol) was administered once a day for 4 days. LPS was administered at a dose of 5 mg/kg on day 2 for a single challenge.

16. EAE Induction

C57BL/6 mice at an age of 7~8 weeks were immunized with 200 µg of $MOG_{35-55}$ in 100 µl of a solution containing 50% complete Freund's adjuvant with 10 mg/ml of the heat-killed H37Ra strain of *Mycobacterium tuberculosis* (Difco). Pertussis toxin (200 ng per mouse) in PBS was administered on the day of immunization and again 48 hrs later. The animals were weighed and examined daily for disease symptoms. Clinical signs of disease were scored using a 0-5 scale, as follows:

0=no clinical sign;
1=limp tail;
2=weakness and incomplete paralysis of one or two hindlimbs;
3=complete hindlimb paralysis;
4=forelimb weakness or paralysis;
5=moribund state or death.

The vehicle (control, distilled water containing 5% DMSO and 40% polyethylene glycol) or ICM was injected daily for 15 days after MOG immunization.

17. Histological Analysis

Mice were anesthetized with diethyl ether, transcardially perfused with cold saline, and then fixed with 4% paraformaldehyde diluted in 0.1 M PBS. Brains or lumbar spinal cords were fixed using 4% PFA for 3 days and then cryoprotected with a 30% sucrose solution for 3 days. Three animals were used per experimental group. The fixed brains and spinal cords were embedded in OCT compound for frozen sectioning and then sectioned coronally at 20 µm. To detect LPS-induced microglial activation, each section was incubated with a rabbit anti-Iba-1 antibody and FluoroMyelin. The sections were visualized directly or incubated with Cy3-conjugated anti-rabbit IgG antibody. Also, the sections were stained with hematoxylin and eosin to assess inflammatory lesions.

<Synthesis of Anti-Inflammatory Pharmaceutical Composition Comprising Benzopyranyl Tetracycle and Assay for Anti-Inflammatory Activity Thereof>

PREPARATION EXAMPLE

Synthesis of 4-substituted-1,2,4-triazolin-3,5-dione

Azadienophile, 4-substituted-1,2,4-triazoline-3,5-dione was synthesized according to the procedure previously reported. Methyl hydrazinocarboxylate was condensed with N-aryl isocyanate, or with N-alkyl amine together with carbonyl diimidazole (CDI) to give a substituted hydrazine carboxylate intermediate. In a fundamental condition, subsequently, the intermediate was subjected to cyclization to form 4-substituted urazole as a stable azadienophile. Then, the azadienophile was oxidized with iodobenzene diacetate (IBD) through in situ Diels-Alder reaction (Reaction Scheme 1).

method of Korean Unexamined Patent Application Publication No. 10-2012-0060957, as illustrated in the following Reaction Scheme 2.

[Reaction Scheme 1] Synthesis Route to 4-Substituted-1,2,4-triazolin-3,5-dione

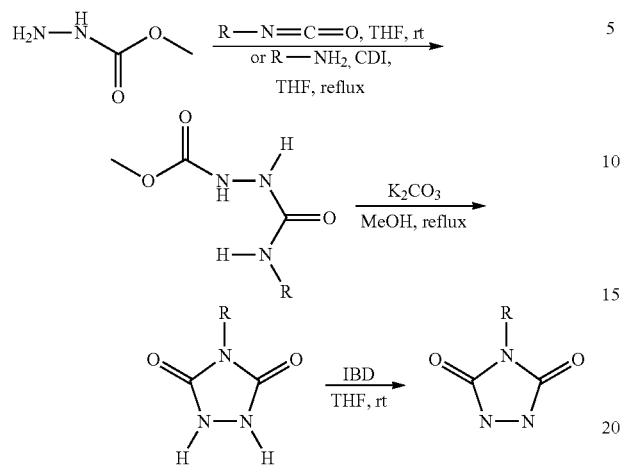

[Reaction Scheme 2] Synthesis Route to Benzopyranyl Tetracycle

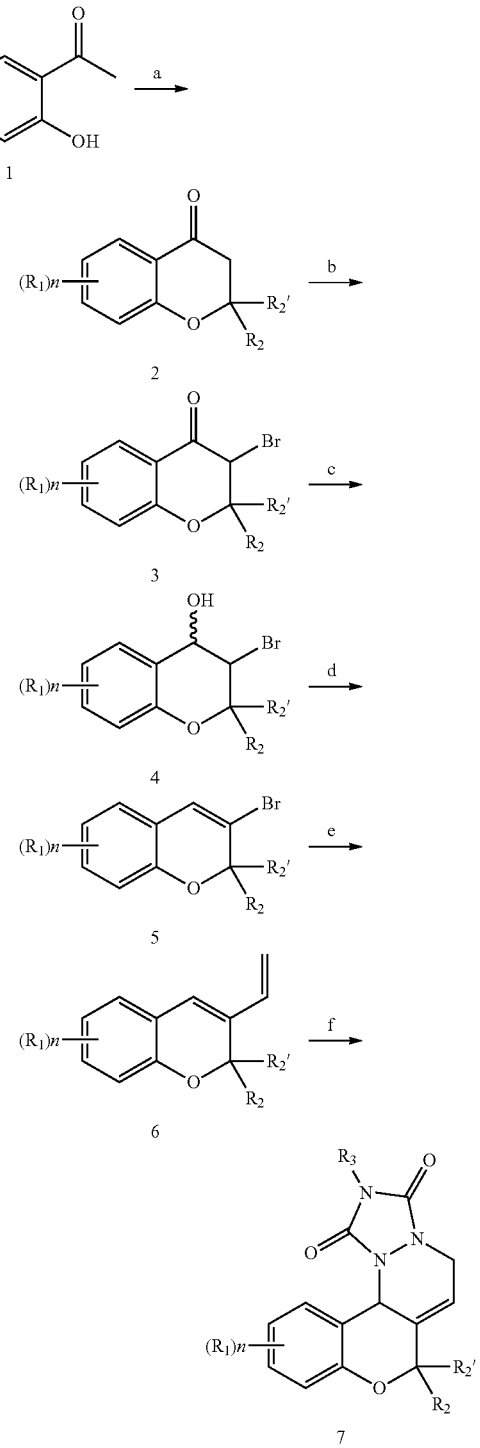

1) Formation of Substituted Hydrazine Carboxylate Intermediate

In an inert atmosphere, methyl hydrazinocarboxylate (1.0 eq.) was dissolved in dry THF with stirring. Aryl isocyanate (1.0 eq.) was sequentially added over 1~2 min to the solution. The resulting mixture was stirred for 2~4 hrs at room temperature to form substituted hydrazine carboxylate as a white precipitate. After completion of the reaction as monitored by TLC, the intermediate was collected by filtration or by drying through simple vaporization. For an intermediate synthesized from N-alkyl amine, methyl hydrazinocarboxylate (1.0 eq.) was also dissolved in dry THF in an inert atmosphere. To this solution, carbonyl diimidazole (CDI, 1.0 eq.) was added, and stirred at room temperature for 30 min. N-alkyl amine (1.0 eq.) was added before stirring overnight at room temperature. After completion of the reaction as monitored by TLC, the reaction mixture was concentrated, and the intermediate was recrystallized at −20° C. from dichloromethane.

2) Cyclization of Intermediate

To a solution of the intermediate (1.0 eq.) in methanol was added potassium carboxylate (2.0 eq.), followed by stirring overnight at room temperature. After completion of the reaction as monitored by TLC, the reaction mixture was concentrated, and the concentrate was re-dissolved in a small volume of water. The acidity of this solution was adjusted to a pH of 3~4, and added with 1 N HCl drop by drop. The desired product was collected by filtration and purified through re-crystallization.

3) Oxidization of Intermediate to Azadienophile

To a solution of 4-substituted-1,2,4-triazolidine-3,5-dione (1.0 eq.) in dry THF was added iodobenzene diacetate (IBD, 1.0 eq.). The reaction mixture was stirred at room temperature during which a color change from transparency to red was an indicator of reaction progress. Completion of the reaction was determined as a complete red color was developed within 15-20 min. The azadienophile 4-substituted-1,2,4-triazoline-3,5-dione can be in situ for Diels-Alder reaction or can be purified by sublimation after removal of the solvent.

Example 1

Synthesis of Benzopyranyl Tetracycle Compounds

The benzopyranyl tetracycle compounds of the present invention were synthesized according to the synthesis In Reaction Scheme 2, each step was conducted as follows:

In step a), ketone and pyrrolidine were added in an ethanol (EtOH) solvent and refluxed; in step b), CuBr2 was added in the mixture solvent EtOAc/CHCl₃/MeOH and refluxed; in step c), NaBH4 was added in an ethanol (EtOH) solvent, and reacted at 40° C.; in step d), p-TsOH was added in toluene solvent and reacted at 70° C.; in step e), the reaction was conducted at 70° C. in the mixture solvent EtOH/toluene/H₂O in the presence of vinylboronic acid dibutyl ester, Na₂CO₃, and Pd(PPh₃)₄; and in step f), the reaction was conducted with triazolinedione at room temperature in a toluene solvent to finally afford benzopyranyl tetracycle compounds.

Compounds represented by the following Chemical Formulas 2 to 51 are benzopyranyl tetracycles, and the compound of Chemical Formula 2 was designated "ICM".

[Chemical Formula 2]

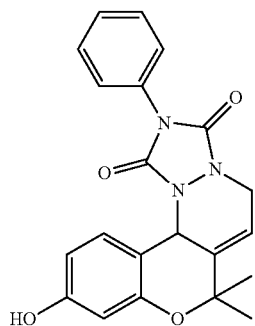

[Chemical Formula 3]

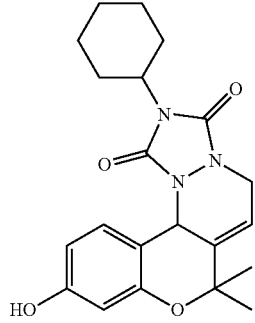

[Chemical Formula 4]

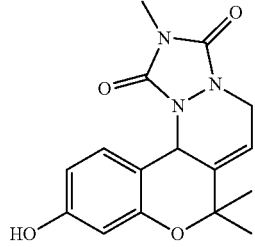

[Chemical Formula 5]

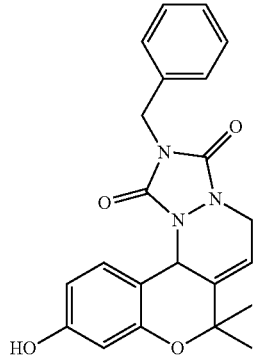

[Chemical Formula 6]

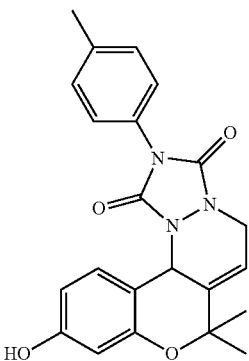

[Chemical Formula 7]

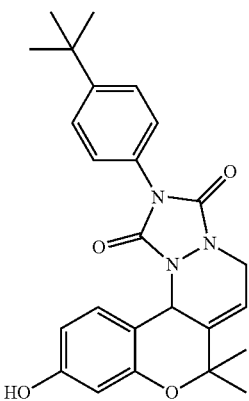

[Chemical Formula 8]

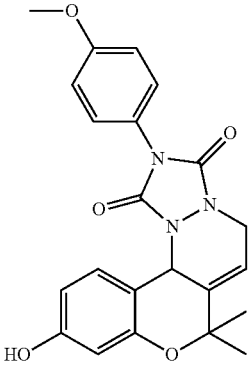

[Chemical Formula 9]

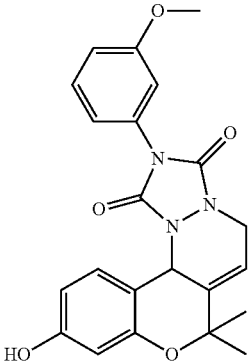

-continued
[Chemical Formula 10]
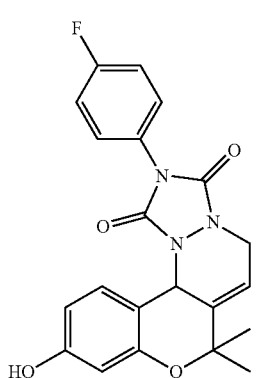
[Chemical Formula 11]
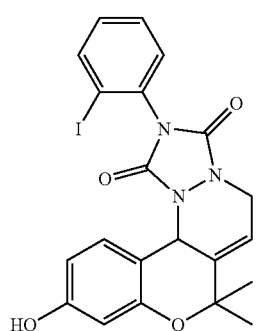
[Chemical Formula 12]
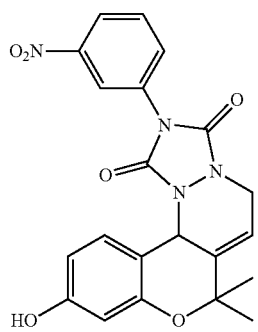
[Chemical Formula 13]
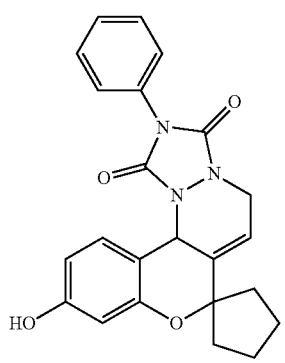
-continued
[Chemical Formula 14]
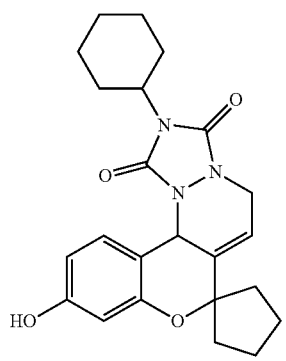
[Chemical Formula 15]
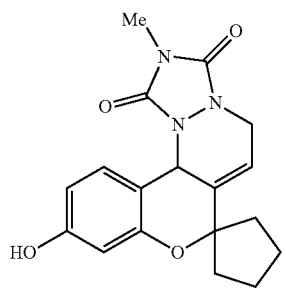
[Chemcial Formula 16]
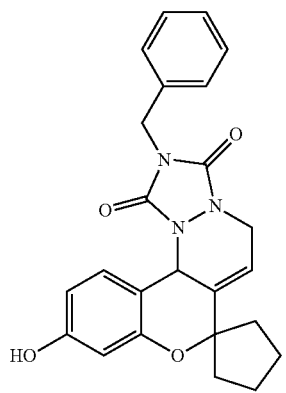
[Chemical Formula 17]
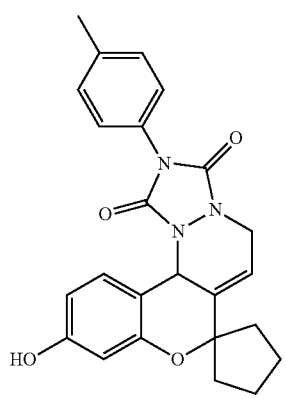

[Chemical Formula 18]
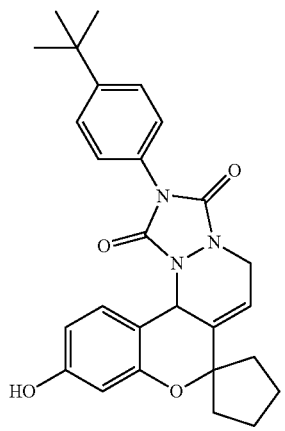
[Chemical Formula 19]
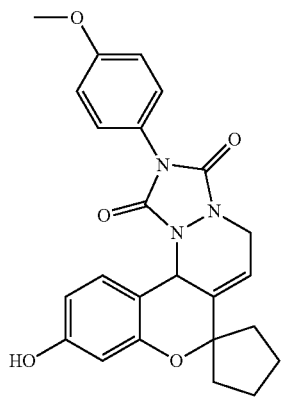
[Chemical Formula 20]
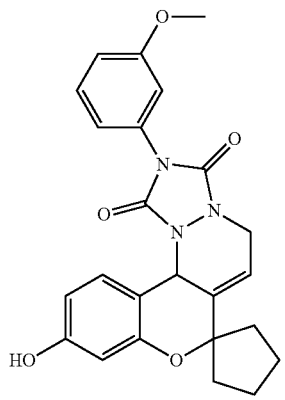
[Chemical Formula 21]
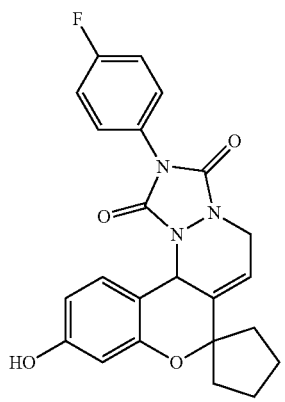
[Chemical Formula 22]
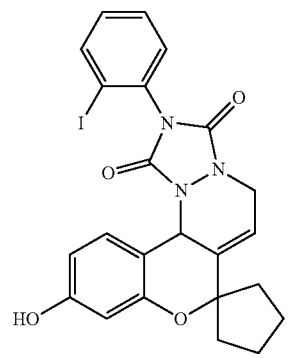
[Chemical Formula 23]
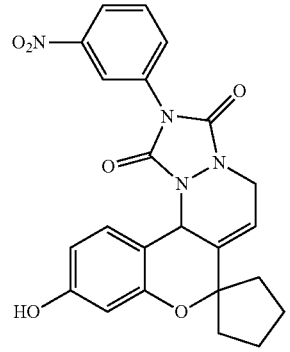
[Chemical Formula 24]
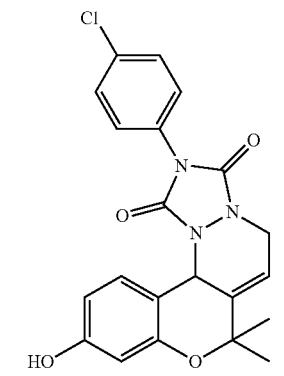
[Chemical Formula 25]
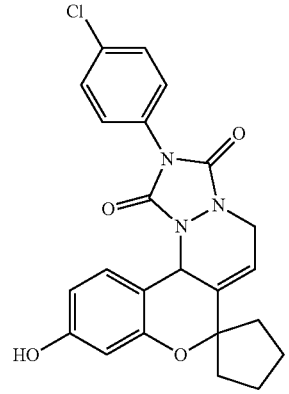

[Chemical Formula 26]
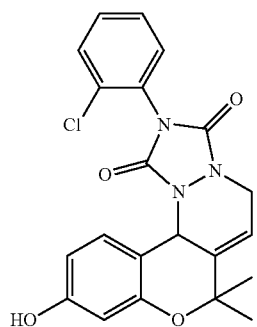
[Chemical Formula 27]
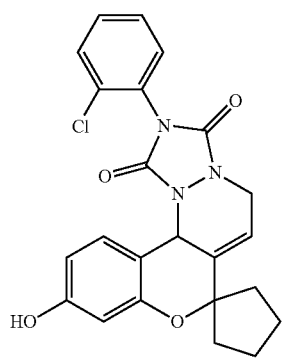
[Chemical Formula 28]
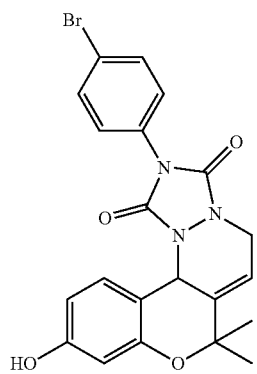
[Chemical Formula 29]
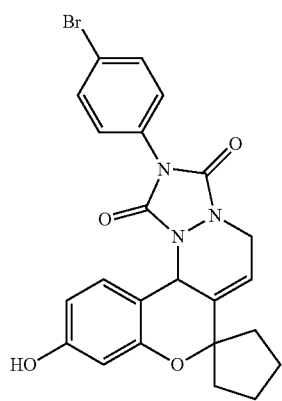
[Chemical Formula 30]
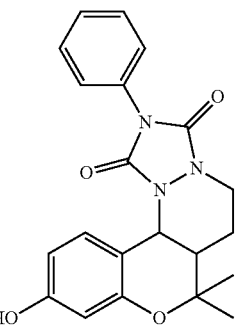
[Chemical Formula 31]
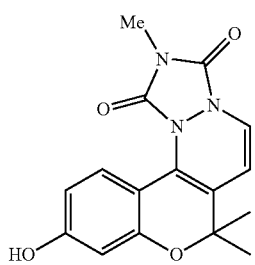
[Chemical Formula 32]
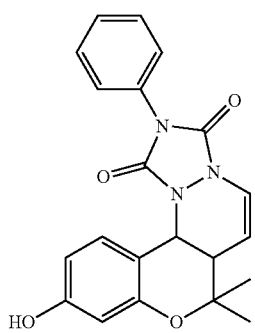
[Chemical Formula 33]
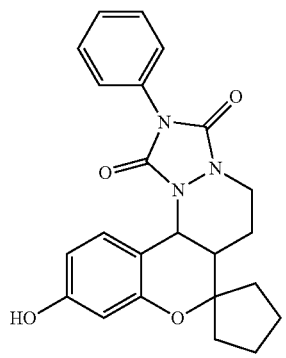
[Chemical Formula 34]
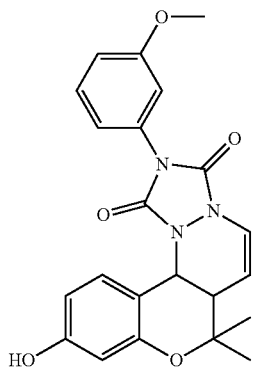

[Chemical Formula 35]
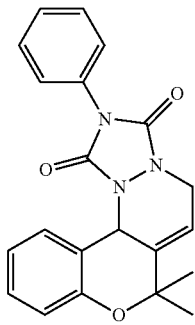
[Chemical Formula 36]
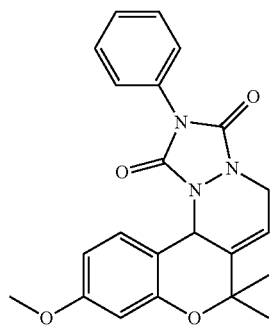
[Chemical Formula 37]
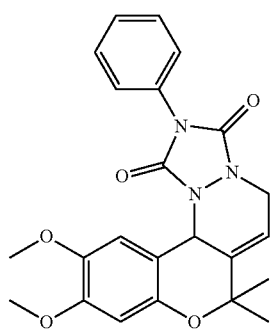
[Chemical Formula 38]
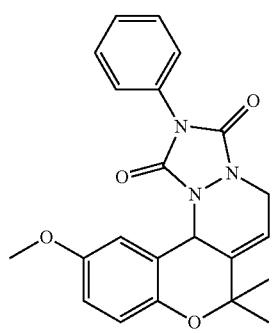
[Chemical Formula 39]
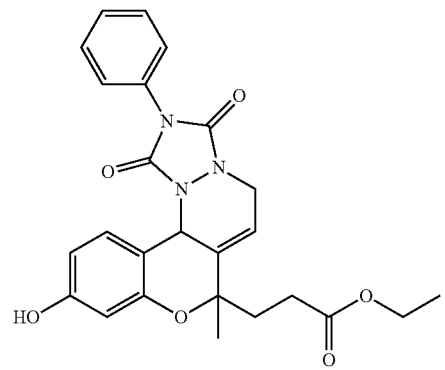
[Chemical Formula 40]
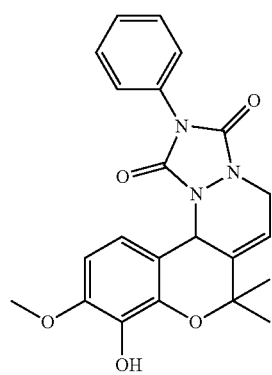
[Chemical Formula 41]
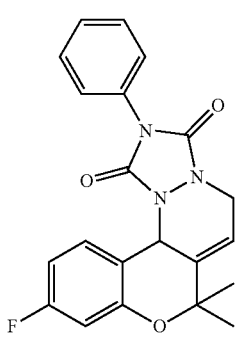
[Chemical Formula 42]
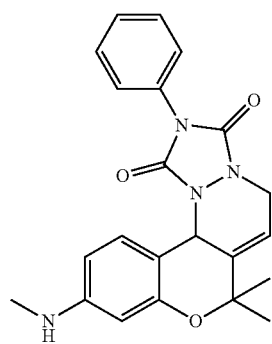

US 9,468,641 B2
[Chemical Formula 43]
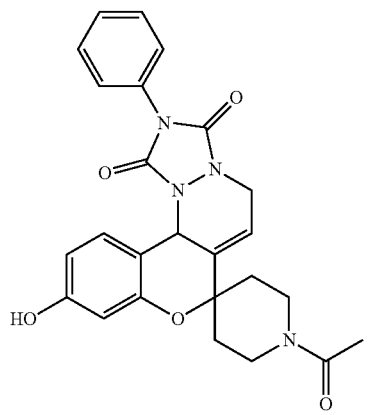
[Chemical Formula 44]
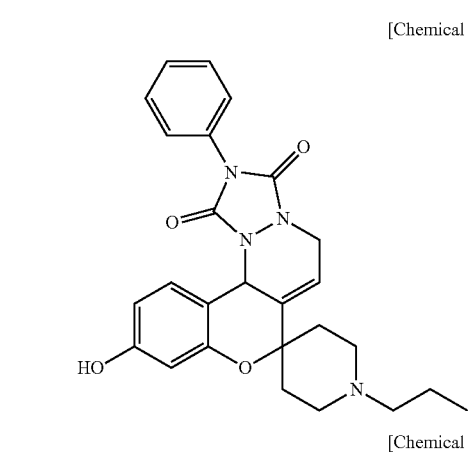
[Chemical Formula 45]
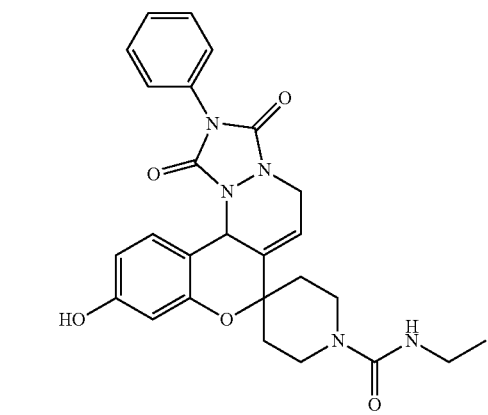
[Chemical Formula 46]
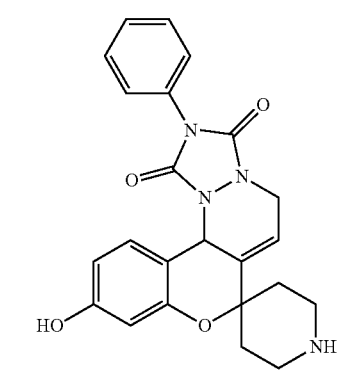
[Chemical Formula 47]
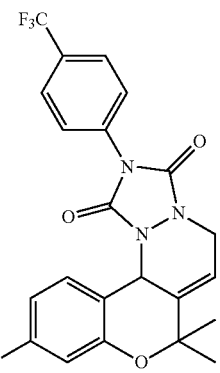
[Chemical Formula 48]
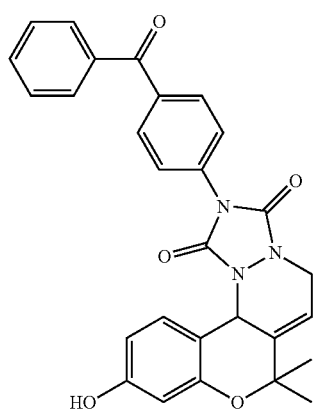
[Chemical Formula 49]
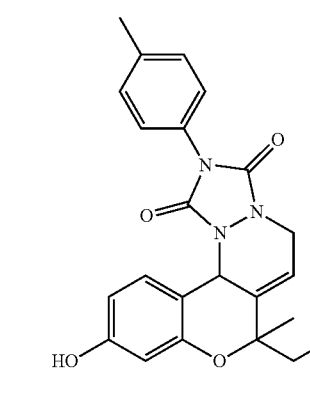
[Chemical Formula 50]
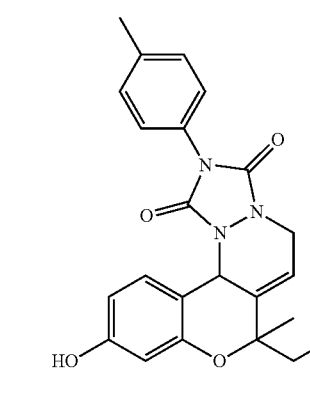

-continued

[Chemical Formula 51]

Test Example 1

Assay for Anti-Inflammatory Effect of ICM in LPS-Induced Neuroblastoma Activation Model 1-1. According to the Griess assay of Reference Example 2, analysis was made of the dose-dependent anti-inflammatory effect of ICM on BV2 cells in the presence or absence of LPS stimulation, and the results are depicted in FIG. 1.

FIG. 1 shows levels (μM) of nitrite released by BV2 cells plotted against the amounts (μM, dose-dependent) of ICM in the presence or absence of LPS stimulation. In FIG. 1, 'LPS(+)' represents for stimulation with LPS while 'LPS(−)' stands for non-LPS stimulation.

As can be seen in FIG. 1, ICM efficiently blocked LPS-induced nitrite release from BV2 microglial cells in a dose-dependent manner, which demonstrates that ICM suppresses inflammatory responses in the microglial cells.

1-2. Anti-inflammatory effects of ICM on BV-2 cells, HAPI cells, primary neuroblastoma, and RAW 264.7 were analyzed as measured by the Griess assay of Reference Example 2, and the results are given in FIG. 2.

Figure 2:
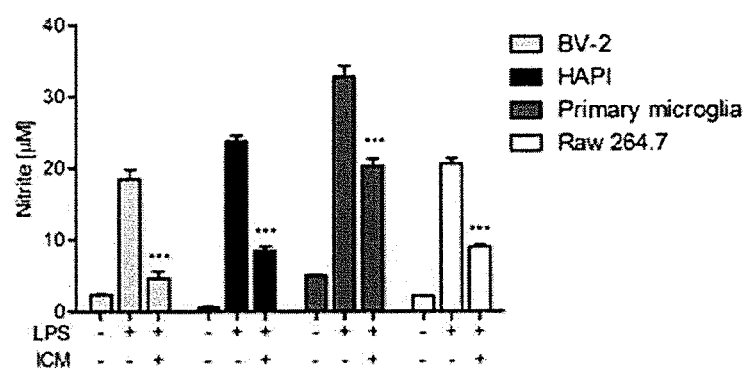
FIG. 2 shows the levels (μM) of nitrite released by BV-2 cells, HAPI cells, Primary neuroblastoma, and RAW 264.7 cells treated with or without ICM in the presence or absence of LPS stimulation.

FIG. 2 show the levels (μM) of nitrite released by BV-2 cells, HAPI cells, Primary neuroblastoma, and RAW 264.7 cells treated with or without ICM in the presence or absence of LPS stimulation. In FIG. 2, treated groups are marked with '+' while non-treated groups are marked with '−'.

As is understood from FIG. 2, ICM was observed to inhibit nitrite release in a broad range of cell lines including microglia, and macrophages as well as BV-2 cells.

1-3. Examination was made of the expression of pro-inflammatory mediators in cells treated with or without ICM in the presence or absence of LPS stimulation according to the RT-PCR of Reference Example 4. The results are depicted in FIG. 3.

Figure 3:
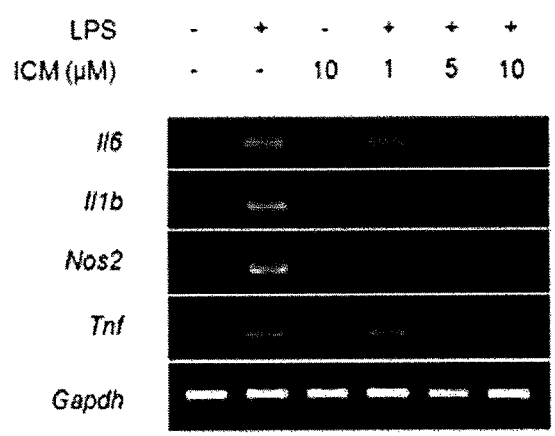
FIG. 3 shows expression levels of Il6, Il1b, Nos2, and Tnf in cells treated with or without ICM in the presence or absence of LPS stimulation.

FIG. 3 shows expression levels of Il6, Il1b, Nos2, and Tnf in cells treated with or without ICM in the presence or absence of LPS stimulation as analyzed by RT-PCR, in which marks '+' and '−' for the LPS row stand for 'treatment' and 'non-treatment', respectively.

As shown in FIG. 3, ICM suppressed the LPS-induced expression of pro-inflammatory genes in a dose-dependent manner, which demonstrates that ICM has a suppressive effect on inflammatory response rather than inhibits nitrite release only.

1-4. LPS-induced secretion of the proinflammatory cytokine TNFα with ICM treatment or non-treatment was measured by ELISA, as described in Reference Example 5. The results are shown in FIG. 4.

Figure 4:
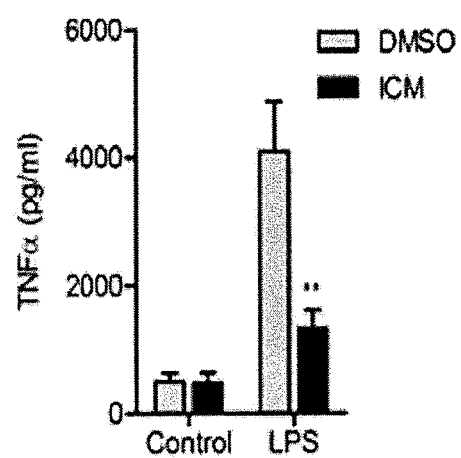
FIG. 4 shows levels (pg/ml) of the proinflammatory cytokine TNFα upon treatment with or without ICM in the presence or absence of LPS stimulation, wherein the control represents a cell group that was not treated with LPS.

FIG. 4 shows levels (pg/ml) of the proinflammatory cytokine TNFα upon treatment with or without ICM in the presence or absence of LPS stimulation. In FIG. 4, the control represents a cell group that was not treated with LPS.

As can be seen in FIG. 4, ICM suppressed LPS-induced secretion of the proinflammatory cytokine, which demonstrates that ICM has a suppressive effect on inflammatory response rather than inhibits nitrite release only.

Figure 5:
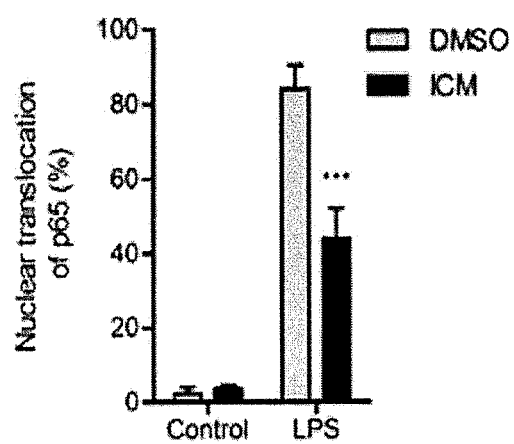
FIG. 5 shows the nuclear translocation of p65(%) in cells treated with or without ICM in the presence or absence of LPS stimulation, wherein the control represents an LPS-non-treated group.

1-5. FIG. 5 shows the nuclear translocation of p65(%) in cells treated with or without ICM in the presence or absence of LPS stimulation, wherein the control represents an LPS-non-treated group.

FIG. 5 shows the nuclear translocation of p65(%) in cells treated with or without ICM in the presence or absence of LPS stimulation, wherein the control represents an LPS-non-treated group.

As is understood from the data of FIG. 5, ICM suppressed NF-κB signaling.

1-6. Examination was made of the effect of ICM on microglial neurotoxicity as analyzed by the coculture of microglial cells and B35-EGFP neuroblastoma cells of Reference Example 7. The results are shown in FIG. 6.

Figure 6:
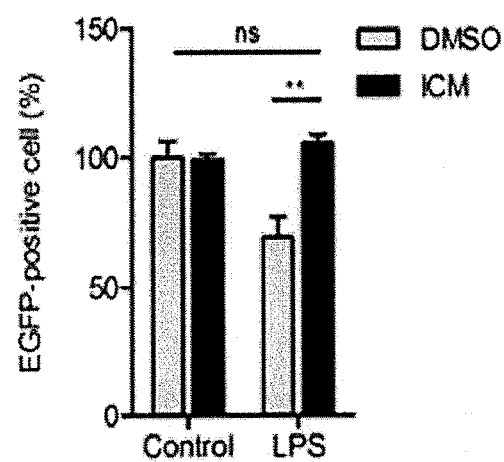
FIG. 6 shows levels of EGFP-positive cells (%) upon treatment with or without ICM in the presence or absence of LPS stimulation, as analyzed for the effect of ICM on neurotoxicity by microglial-neuroblastoma coculture.

FIG. 6 shows levels of EGFP-positive cells (%) upon treatment with or without ICM in the presence or absence of LPS stimulation, as analyzed for the effect of ICM on neurotoxicity by microglial-neuroblastoma coculture.

Example 2

Introduction of Probe to ICM (ICM-BP)

For use in FITGE (Fluorescence Difference in Two Dimensional Gel Electrophoresis) by which intracellular target proteins can be effectively identified, a hit compound-based probe was synthesized.

Figure 7:
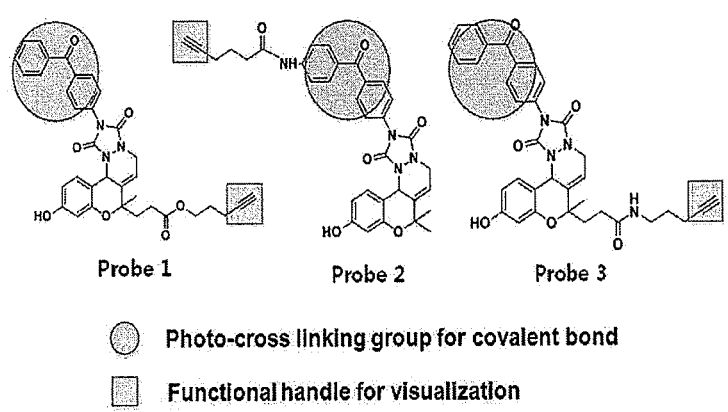
FIG. 7 shows chemical structures of ICM compounds to which probes are introduced.
Figure 8:
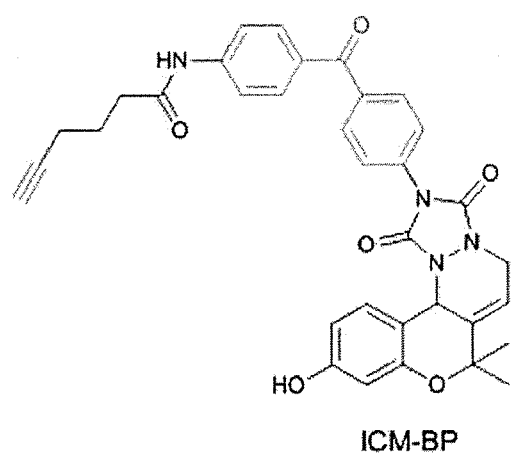
FIG. 8 shows the chemical structure of ICM-BP.

The hit compound-based probe is required to contain both a photoactive moiety and a bio-orthogonal functional moiety. In many experiments with various kinds and locations of photoactive moieties and functional moieties, many probes were introduced into benzopyranyl tetracycles. The most active among them were those in which benzophenone is embedded as the photoactivatable crosslinking moiety while a terminal alkyne group was incorporated as the bio-orthogonal functional moiety. Examples of the probe-introduced ICM compounds are shown in FIG. 7. The highest activity was found in Probe II as measured by NO (nitric oxide) assay. In subsequent experiments for target protein identification, Probe II (hereinafter referred to as "ICP-BP", FIG. 8) was used.

Test Example 2

Identification of Cellular Target Protein by ICM 2-1. The anti-inflammatory effect of ICM-BP on BV-2 cells was analyzed according to the Griess assay of Reference Example 2. The results are given in FIG. 9.

Figure 9:
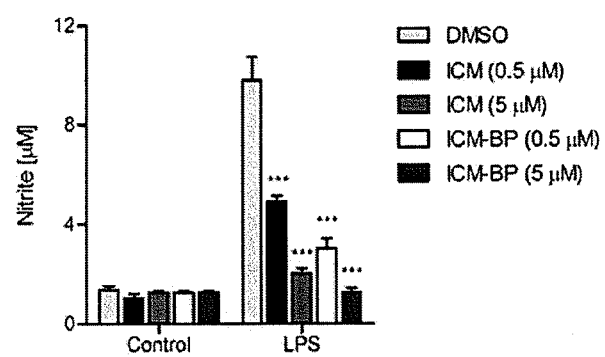
FIG. 9 shows levels (μM) of nitrite released by BV2 cells treated with or without ICM or ICM-BP after LPS stimulation.

FIG. 9 shows levels (μM) of nitrite released by BV2 cells treated with or without ICM or ICM-BP after LPS stimulation.

As can be seen in FIG. 9, ICM-BP is valuable as a probe because it exhibited inhibitory activity at a level comparable to that of the original compound ICM.

2-2. After UV-induced labeling of ICM-BP to cellular target proteins, ICM-BP-labeled proteomes were analyzed by the In-gel analysis of Reference Example 8, and the results are given in FIG. 10.

Figure 10:
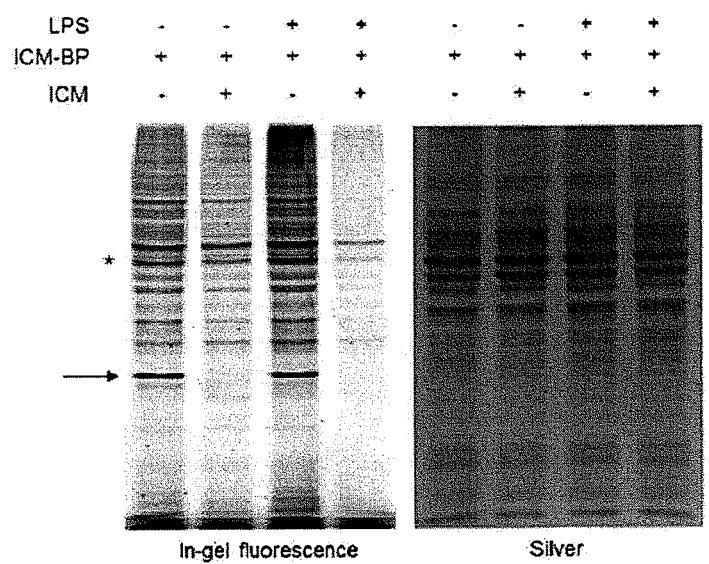
FIG. 10 shows 1-D gel electrophoresis patterns of ICM-BP-labeled proteins by in-gel fluorescence (left panel) and by silver staining for proving the same amount of loaded proteins (right panel), in which ICM is used as a competitor to effectively exclude non-specific proteins.

FIG. 10 shows 1-D gel electrophoresis patterns of ICM-BP-labeled proteins by in-gel fluorescence (left panel) and by silver staining for proving the same amount of loaded proteins (right panel), in which ICM is used as a competitor to effectively exclude non-specific proteins.

As can be seen in FIG. 10, two distinct bands for ICM are designated by both the asterisk and the arrow regardless of LPS stimulation. Hence, the proteins in these two bands were compressed as a potential candidate group of the target protein. The protein in the band indicated by the arrow was further analyzed as it outcompeted at a lower concentration of ICM more effectively in a dose-dependent competitive assay.

2-3. Target identification was carried out with ICM-BP using 2-D gel analysis as described in the In-gel analysis of Reference Example 8. The results are shown in FIG. 11.

Figure 11:
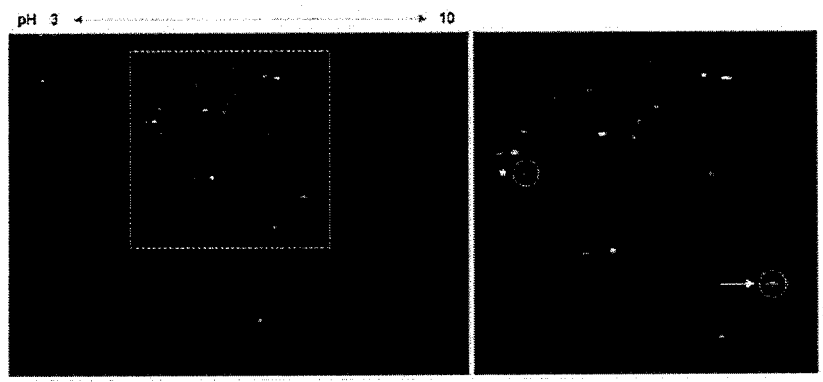
FIG. 11 shows fluorescent images of ICM-BP-labeled proteins with and without ICM competition that were treated with Cy3-azide (green) and Cy5-azide (red), respectively, as analyzed by 2-D gel analysis.

FIG. 11 shows fluorescent images of ICM-BP-labeled proteins with and without ICM competition that were treated withCy3-azide (green) and Cy5-azide (red), respectively, as analyzed by 2-D gel analysis.

In FIG. 11, the specific binding of ICM-BP to the target protein is expressed by red spots.

Figure 12:
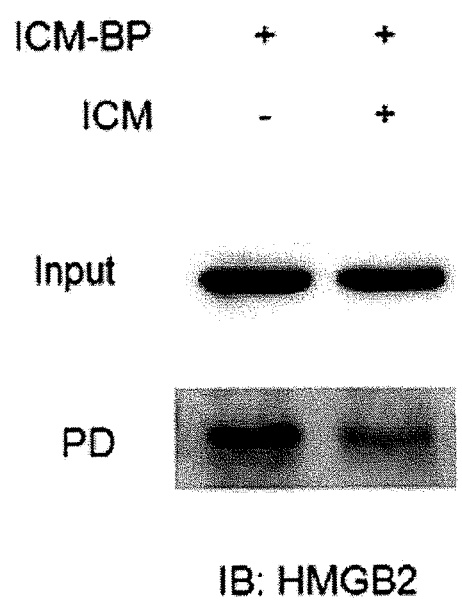
FIG. 12 is an image of immunoblots, showing that HMGB2 efficiently bound ICM-BP whereas ICM as a soluble competitor markedly lowered the level of binding for HMGB2, which confirmed specific interaction between ICM-BP and HMGB2.

2-4. To assess the specific binding event of ICM-BP with HMGB2, an pull-down assay of Reference Example 9 was performed with a biotin-labelled protein and streptavidin bead. ICM-BP (5 μM) with or without ICM competition (20 μM) was subjected to pull-down assay, sample were analyzed by electrophoresis, and immunoblotting for HMGB2 followed thereafter. The results are given in FIG. 12. FIG. 12 is an image of immunoblots, showing that HMGB2 efficiently bound ICM-BP whereas ICM as a soluble competitor markedly lowered the level of binding for HMGB2, which confirmed specific interaction between ICM-BP and HMGB2.

As shown in FIG. 12, ICM-BP was proven to bind specifically to HMGB2.

Test Example 3

Functional Validation of HMGB as Taget of ICM 3-1. Analysis for binding mode and dissociation constant between ICM and purified HMGB2 protein was made, and the results are given in FIG. 13.

Figure 13:
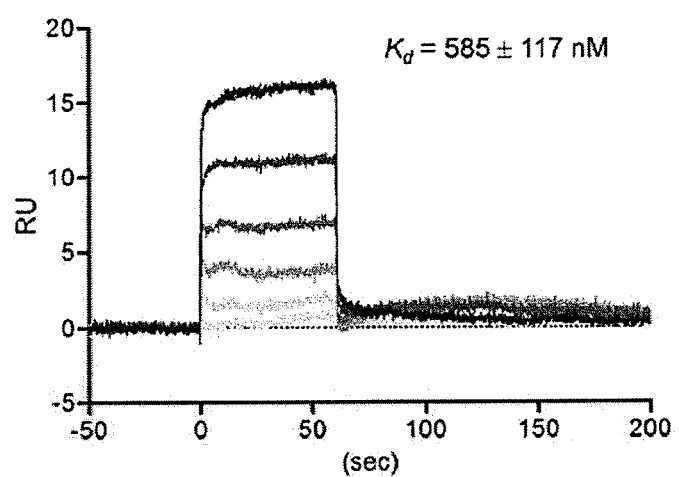
FIG. 13 is a sensorgram showing response units for the binding, with exposure to 1, 15, 30, 50, 75, and 100 μM ICM (white→black, 1→100 μM)

FIG. 13 is a sensorgram showing response units for the binding, with exposure to 1, 15, 30, 50, 75, and 100 μM ICM (white→black, 1→100 μM).

As can be seen in FIG. 13, the binding strength increased with an increase in ICM concentration, demonstrating that ICM binds directly to HMGB.

3-2. RT-PCR was performed in BV-2 cells with siRNA-mediated HMGB2 knockdown (control: Gapdh) according to the siRNA-mediated knockdown assay of Reference Example 12. The results are given in FIG. 14.

Figure 14:
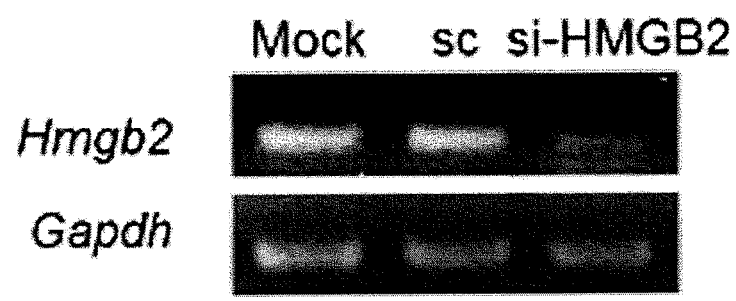
FIG. 14 shows gene patterns of BV-2 cells transfected with a mock (Mock, transfection reagent without siRNA), scrambled siRNA (sc), or siRNA for HMGB2 (si-RNA), as analyzed by RT-PCR.

FIG. 14 shows gene patterns of BV-2 cells transfected with a mock (Mock, transfection reagent without siRNA), scrambled siRNA (sc), or siRNA for HMGB2 (si-RNA), as analyzed by RT-PCR.

As is understood from the data of FIG. 14, si-HMGB2 transfection downregulated the expression of HMGB2 RNA.

3-3. According to the Griess assay of Reference Example 2, analysis was made of the inhibition of HMGB2 knockdown against LPS-induced nitrite release in BV-2 cells. The results are shown in FIG. 15.

Figure 15:
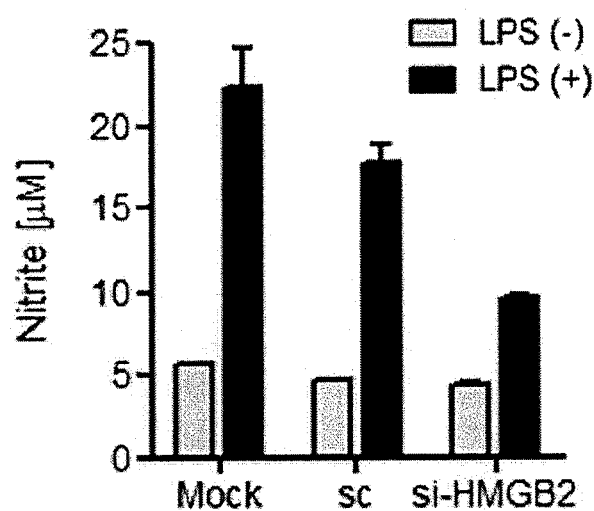
FIG. 15 shows levels (μM) of nitrite released by BV-2 cells transfected with siRNA for HMGB2, scrambled siRNA (sc), and a mock (Mock) in the presence (+) or absence (−) of LPS stimulation.

FIG. 15 shows levels (μM) of nitrite released by BV-2 cells transfected with siRNA for HMGB2, scrambled siRNA (sc), and a mock (Mock) in the presence (+) or absence (−) of LPS stimulation.

As can be seen in FIG. 15, HMGB2 knockdown inhibited LPS-induced nitrite release, demonstrating that HMGB2 plays an important role in mediating an inflammatory response in microglial cells.

3-4. The anti-inflammatory effect of ICM on BV-2 cells was analyzed by the Griess assay of Reference Example 2, with normalization to the control DMSO treatment. The results are shown in FIG. 16.

Figure 16:
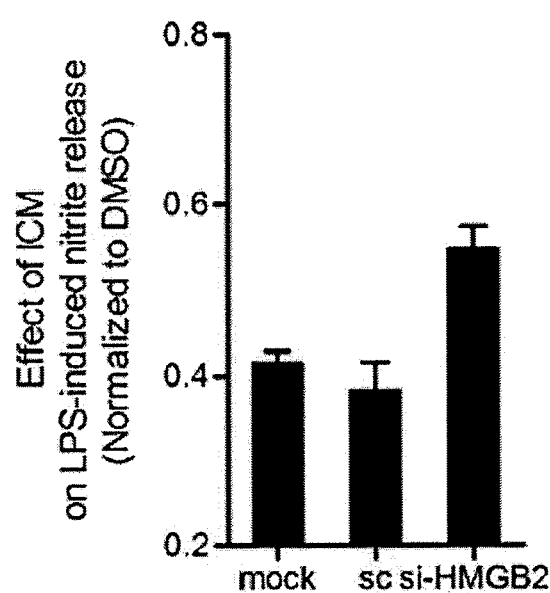
FIG. 16 is a graph showing the anti-inflammatory effect of ICM on LPS-induced nitrite release in BV-2 cells, with normalization to the individual DMSO treatments (the level of nitrite release upon ICM treatment divided by that of nitrite release upon DMSO treatment), wherein Mock stands for control transfection, sc for transfection with scrambled siRNA, and si-RNA for transfection with siRNA for HMGB2.

FIG. 16 is a graph showing the anti-inflammatory effect of ICM on LPS-induced nitrite release in BV-2 cells, with normalization to the individual DMSO treatments (the level of nitrite release upon ICM treatment divided by that of nitrite release upon DMSO treatment), wherein Mock stands for control transfection, sc for transfection with scrambled siRNA, and si-RNA for transfection with siRNA for HMGB2.

As is apparent from FIG. 16, a higher level of nitrite was released from the cells with HGMB2 knockdown by ICM treatment than the controls (mock, sc transfection, ICM treatment). That is, the anti-inflammatory effect of ICM was decreased by HMGB2 knockdown, indicating that ICM exhibits an HMGB-dependent anti-inflammatory effect.

Test Example 4

Study on Inhibition Mechanism of ICM against HMGB2-Mediated Inflammation 4-1. ICM was observed to perturb the translocation of HMGB2 from the nucleus to the cytoplasm and extracellular milieu, as analyzed by the subcellular fractionation and secretion analysis of Reference Example 13. The results are given in FIG. 17.

Figure 17:
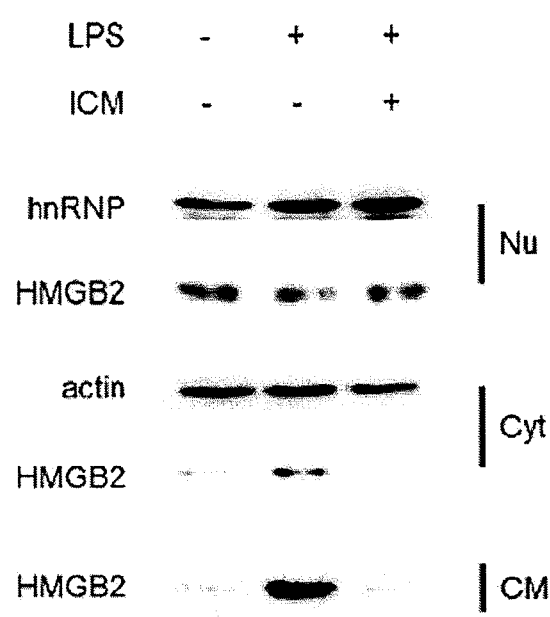
FIG. 17 shows protein patterns as analyzed by electrophoresis and western blotting.

FIG. 17 shows protein patterns as analyzed by electrophoresis and western blotting, wherein Nu stands for nucleus, Cyt for cytoplasm, and CM for extracellular milieu (actin and hnRNP were used as controls).

As is understood from the data of FIG. 17, LPS stimulation induced the translocation of HMGB2 from the nucleus to the cytoplasm and further to extracellular milieu, and the translocation was suppressed by ICM.

4-2. ICM was observed to suppress the LPS-induced post-translational modification of HMGB2 and HMGB1 (phosphorylation and acetylation) as analyzed by the subcellular fractionation and secretion analysis of Reference Example 13 and the immunoprecipitation analysis of Reference Example 14. The results are shown in FIG. 18.

Figure 18:
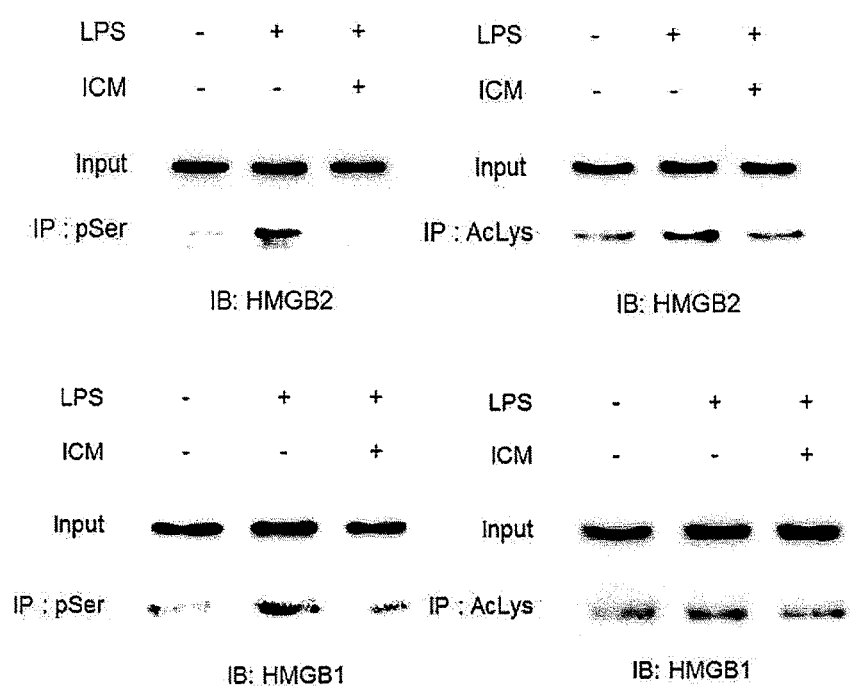
FIG. 18 shows protein patterns as analyzed by electrophoresis and western blotting.

FIG. 18 shows protein patterns as analyzed by electrophoresis and western blotting.

As can be seen in FIG. 18, LPS stimulation induced the phosphorylation on serine residues and acetylation on lysine residues of HMGB2 and HMGB1, but the post-translational modification was suppressed by ICM.

Test Example 5

Animal Test (ICM)

5-1. Suppressive effects of ICM on LPS-mediated microglial activation were quantitatively analyzed in mouse brain parts including the cortex, the hippocampus and the substantia nigra as described in the histological analysis of Reference Example 17, and the results are given in FIG. 19.

Figure 19:
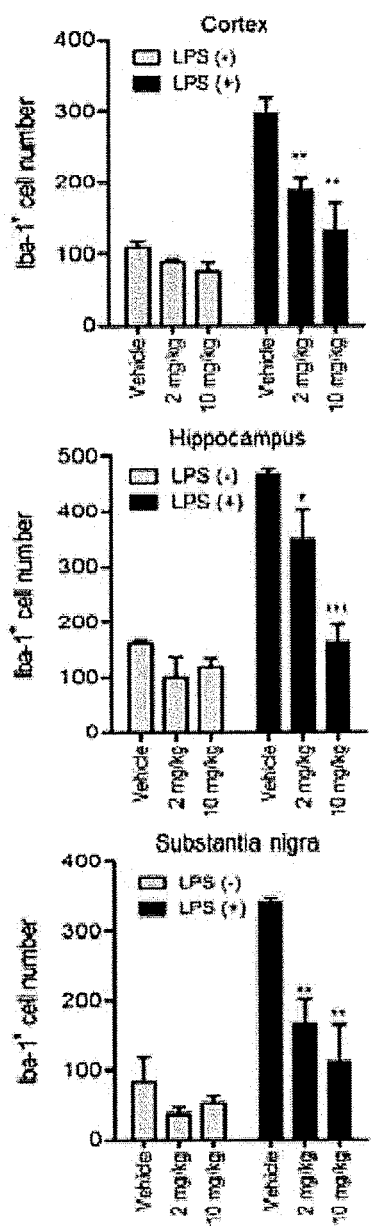
FIG. 19 shows the suppression of glial activation by ICM administration in the cortex, substantia nigra and hippocampus of mice injected with or without LPS in terms of Iba-1+ cell number.

FIG. 19 shows the suppression of glial activation by ICM administration in the cortex, substantia nigra and hippocampus of mice injected with or without LPS in terms of Iba-1+ cell number (Vehicle for control; ICM was administered at a dose of 2 and 10 mg/kg body weight of mouse).

As can be understood in FIG. 19, ICM effectively blocked LPS-mediated microglial activation in all the brain parts.

5-2. To evaluate the protective role of ICM in the pathogenesis of neuroinflammatory disease, EAE clinical scores were counted in a mouse experimental auto-immune encephalitis (EAE) model that was administered with ICM after MOG immunization, as described in the EAE induction of Reference Example 16. The results are depicted in FIG. 20.

Figure 20:
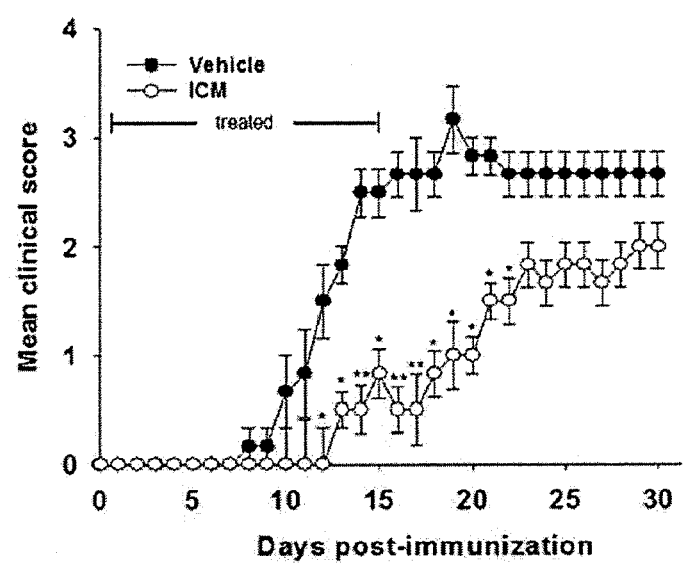
FIG. 20 is a graph in which mean clinical scores on a 0-5 scale obtained by EAE induction are plotted against days after immunization with ICM or vehicle, as described in Reference Example 16.

FIG. 20 is a graph in which mean clinical scores on a 0-5 scale obtained by EAE induction are plotted against days after immunization with ICM or vehicle (5% DMSO, 40% polyethylene glycol in distilled water, control).

As can be seen in FIG. 20, the clinical score increased with EAE induction, and was reduced with ICM treatment, demonstrating the in vivo validation of the anti-inflammatory activity of ICM.

5-3. To examine the activation of microglia and the inflammatory response, histological analysis was performed on the mice, as described in Reference Example 17. Frozen sections of spinal cords were stained with FluoroMyelin for myelin and an anti-Iba-1 antibody for microglial activation. The results are given in FIG. 21.

Figure 21:
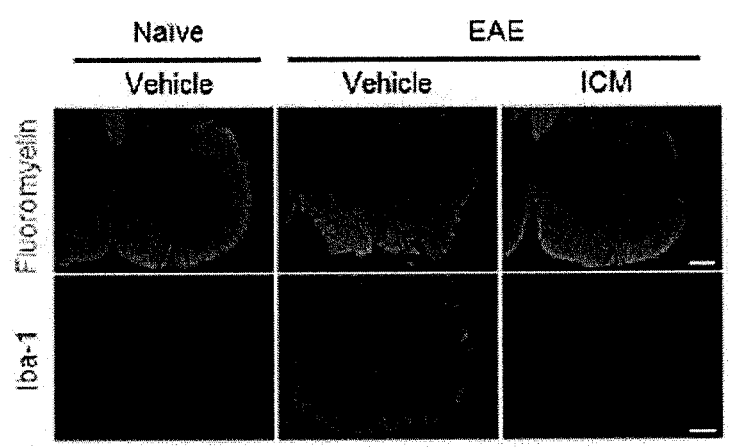
FIG. 21 shows fluorescent images of FluoroMyelin- and anti-Iba-1 antibody-stained spinal cord sections from the EAE model, the normal mice (nave) and the control (vehicle)

FIG. 21 shows fluorescent images of FluoroMyelin- and anti-Iba-1 antibody-stained spinal cord sections from the EAE model, the normal mice (naïve) and the control (vehicle).

As is understood in FIG. 21, microglial activation was induced in the spinal cords of the EAE model, and was clearly suppressed by ICM treatment.

5-4. Likewise, mice at the peak of disease was euthanized and underwent histological analysis of Reference Example 17 with H&E (hematoxylin and eosin) staining. The results are shown in FIG. 22.

Figure 22:
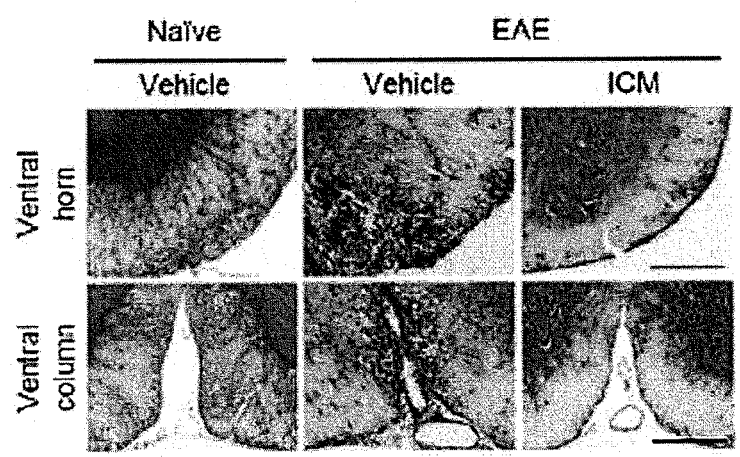
FIG. 22 shows pathological symptoms through images of H&E (hematoxylin and eosin)-stained lumbar spinal cord sections excised from the mice 15 days after EAE induction.

FIG. 22 shows images of H&E (hematoxylin and eosin)-stained lumbar spinal cord sections excised from the mice 15 days after EAE induction.

As can be seen in FIG. 22, the inflammatory lesions in EAE spinal cords were substantially attenuated by ICM treatment.

5-5. Microglial cells isolated from the brain of EAE mice were subjected to analysis of the mRNA levels of proinflammatory cytokines and chemokines by RT-PCR. The results are given in FIG. 23.

Figure 23:
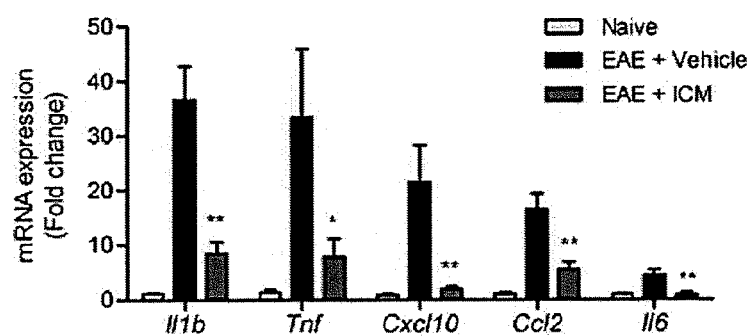
FIG. 23 is a graph showing the mRNA levels of proinflammatory markers Tnf, Cxcl10, Ccl2, Il6), as measured by RT-PCR.

FIG. 23 is a graph showing the mRNA levels of proinflammatory markers (lllb, Tnf, Cxcl10, Ccl2, Il6), as measured by RT-PCR.

As is understood in FIG. 23, levels of proinflammatory cytokines and chemokines were increased in microglia of the EAE model, but decreased in the ICM-treated group.

5-6. HMGB2 levels in the cerebrospinal fluid and serum and of EAE mice were measured by ELISA. The results are given in FIG. 24.

Figure 24:
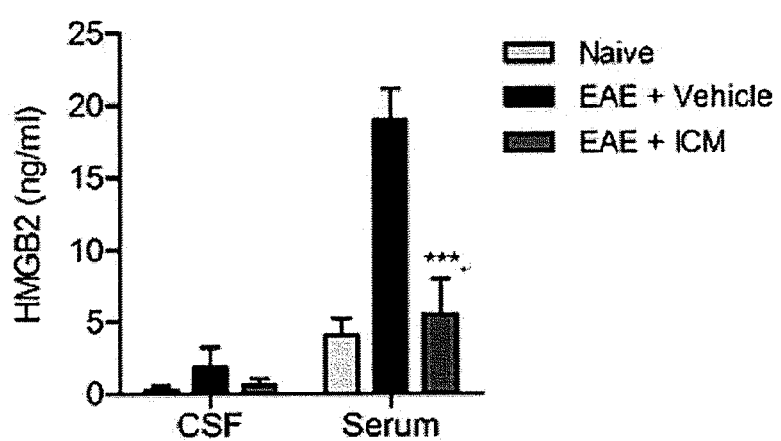
FIG. 24 shows HMGB2 levels in cerebrospinal fluid (CSF) and serum of naïve mice, and EAE mice treated with ICM or vehicle, as analyzed by ELISA.

FIG. 24 shows HMGB2 levels in cerebrospinal fluid (CSF) and serum of naïve mice, and EAE mice treated with ICM or vehicle.

As can be seen in FIG. 24, HMGB2 levels were elevated in cerebrospinal fluid and serum of the EAE model, but ICM treatment effectively suppressed the release of HMGB2 into body fluids after EAE induction, indicating that ICM inhibits the role as a proinflammatory cytokine of HMGB2.

5-7. The effect of ICM on the increased level of HMGB2 and HMGB1 in the EAE model was examined by immunofluorescence analysis using co-staining with an antibody to HMGB2 or HMGB1, and an anti-Iba-1 antibody. The results are shown in FIG. 25.

Figure 25:
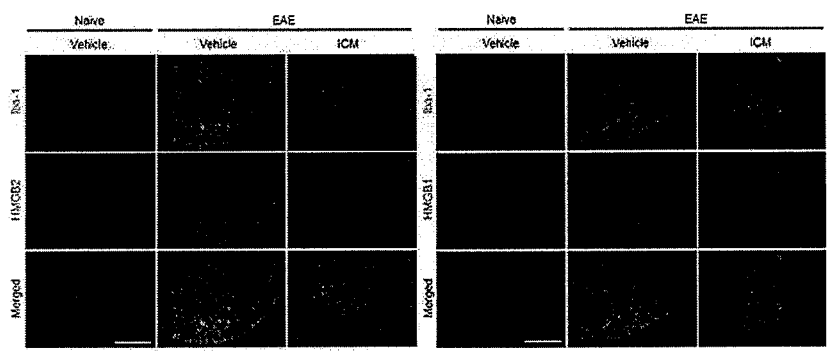
FIG. 25 shows fluorescence images of spinal cord sections co-stained with an antibody to HMGB2 or HMGB, together with an anti-Iba-1 antibody.

FIG. 25 shows fluorescence images of spinal cord sections co-stained with an antibody to HMGB2 or HMGB, together with an anti-Iba-1 antibody. As can be seen, ICM treatment effectively reduced the EAE-induced increase of HMGB1 or HMGB2 levels. In addition, the HMGB increase was also observed in microglia cells as revealed by the co-staining.

5-8. Examination was made of the neuroprotective effect of ICM in the EAE model. For this, immunofluorescence analysis for neuronal dendrites and axons in the ventral horn and ventral column of the EAE model was performed using microtubule-associated protein-2 (MAP-2) antibody. The results are given in FIG. 26.

Figure 26:
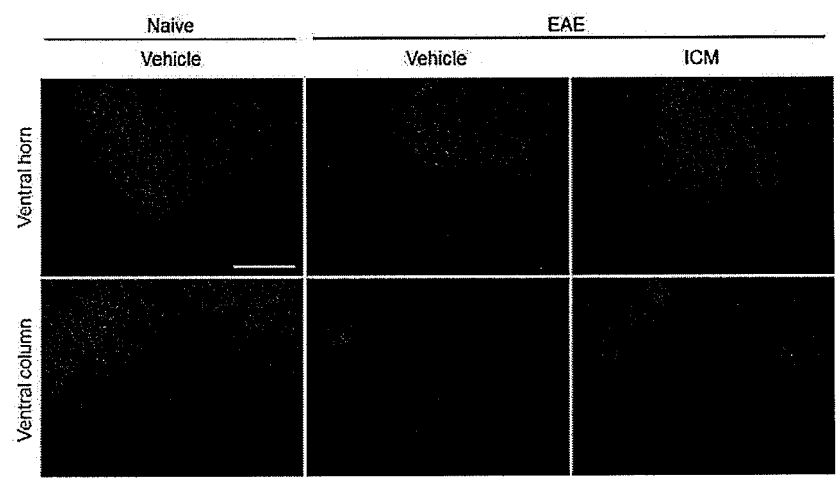
FIG. 26 shows fluorescence images of MAP-2 immunodetected in the ventral horn and ventral column of the EAE model.

FIG. 26 shows fluorescence images of MAP-2 immunodetected in the ventral horn and ventral column of the EAE model.

As can be seen in FIG. 26, MAP-2 levels were decreased in the EAE model, but were effectively recovered by ICM administration. These results indicate the neuroprotective effect of ICM.

5-9. The spinal cord from the EAE model was subjected to immunohistochemistry and immunofluorescence analysis using an antibody to myelin basic protein (MBP), which is marker for myelination, so as to evaluate myelin integrity. The results are given in FIG. 27.

Figure 27:
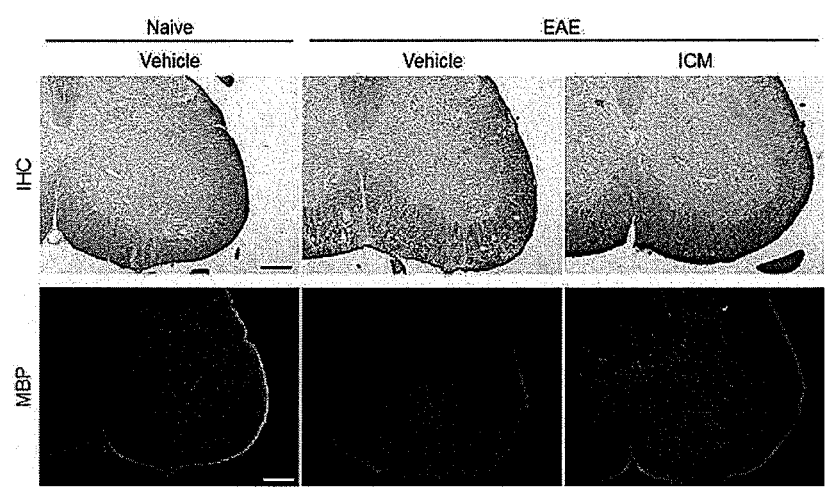
FIG. 27 shows immunofluorescence images of spinal cord sections stained with the anti-MBP antibody. As can be seen, ICM treatment suppresses the demyelination in the EAE model, which demonstrates the neuroprotective activity of ICM.

FIG. 27 shows immunofluorescence images of spinal cord sections stained with the anti-MBP antibody. As can be seen, ICM treatment suppresses the demyelination in the EAE model, which demonstrates the neuroprotective activity of ICM.

Test Example 6

Assay for Anti-Inflammatory Effect of Benzopyranyl Tetracycles in LPS-Induced Neuroblastoma Activation Model Nitrite levels released from BV-2 cells treated with the compounds of Chemical Formulas 3 to 51 were analyzed according to the Griess assay of Reference Example 2. The results are summarized in Table 1, below.

In Table 1, inhibitory activities of compounds represented by Chemical Formulas 3 to 36, 39, 47 to 49, and 51 against nitrite production are expressed as percentages of the nitrite level produced upon DMSO treatment (100%).

TABLE 1

| Cpd. | NO inhibition (%) |
| --- | --- |
| Chemical Formula 3 | 38.0 |
| Chemical Formula 4 | 75.0 |
| Chemical Formula 5 | 63.0 |
| Chemical Formula 6 | 41.8 |
| Chemical Formula 7 | 92.1 |
| Chemical Formula 8 | 77.7 |
| Chemical Formula 9 | 90.8 |
| Chemical Formula 10 | 76.4 |
| Chemical Formula 11 | 55.2 |
| Chemical Formula 12 | 70.4 |
| Chemical Formula 13 | 70.4 |
| Chemical Formula 14 | 48.8 |

TABLE 1-continued

| Cpd. | NO inhibition (%) |
|---|---|
| Chemical Formula 15 | 41.4 |
| Chemical Formula 16 | 53.2 |
| Chemical Formula 17 | 72.1 |
| Chemical Formula 18 | 99.7 |
| Chemical Formula 19 | 58.3 |
| Chemical Formula 20 | 63.0 |
| Chemical Formula 21 | 58.7 |
| Chemical Formula 22 | 67.1 |
| Chemical Formula 23 | 81.5 |
| Chemical Formula 24 | 22.3 |
| Chemical Formula 25 | 44.0 |
| Chemical Formula 26 | 57.1 |
| Chemical Formula 27 | 44.8 |
| Chemical Formula 28 | 58.4 |
| Chemical Formula 29 | 44.0 |
| Chemical Formula 30 | 12.6 |
| Chemical Formula 31 | 12.1 |
| Chemical Formula 32 | 24.9 |
| Chemical Formula 33 | 41.8 |
| Chemical Formula 34 | 4.9 |
| Chemical Formula 35 | 1.2 |
| Chemical Formula 36 | 3.2 |
| Chemical Formula 39 | 44.9 |
| Chemical Formula 47 | 36.0 |
| Chemical Formula 48 | 65.5 |
| Chemical Formula 49 | 63.2 |
| Chemical Formula 51 | 6.2 |

Effectively inhibitory of the post-translational modification of the inflammation mediator HMGB, the compound of Chemical Formula 1 in accordance with the present invention exhibits superior anti-inflammatory activity, and thus can be applied to a pharmaceutical composition that is very effective for the treatment and prevention of inflammation-related diseases.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. A method of treating inflammation, comprising: administering to a subject in need of treatment of inflammation a therapeutically effective amount of an anti-inflammatory pharmaceutical composition, wherein the anti-inflammatory pharmaceutical composition comprises a compound represented by the following Chemical Formula 1 as an active ingredient:

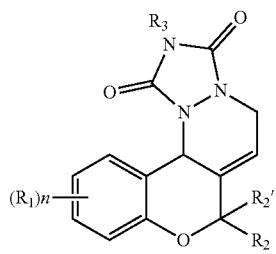

[Chemical Formula 1]

wherein, n of $(R_1)n$ is an integer of 1 to 4, with the proviso that when n is 2 or greater, $R_1$, which is identical or different, each is independently a hydrogen atom; hydroxy; halogen; C1~C6 linear or branched alkyl; C3~C10 cycloalkyl; C1~C6 linear or branched alkoxy; C2~C20 heterocycloalkyl containing N, O or S as a heteroatom; phenyl, unsubstituted or substituted with at least one selected from the group consisting of a halogen atom, amino, nitryl, nitro, C1~C30 alkyl, C2~C30 alkenyl, C1~C30 alkoxy, C3~C30 cycloalkyl, C3~C30 heterocycloalkyl containing N, O or S as a heteroatom, C6-C30 aryl, and C5-C30 heteroaryl containing N, O or S as a heteroatom; benzyl, unsubstituted or substituted with at least one selected from the group consisting of a halogen atom, amino, nitryl, nitro, C1~C30 alkyl, C2~C30 alkenyl, C1~C30 alkoxy, C3~C30 cycloalkyl, C3~C30 heterocycloalkyl containing N, O or S as a heteroatom, C6~C30 aryl, and C5~C30 heteroaryl containing N, O or S as a heteroatom; benzoyl; C1~C30 alkyl amino; C2~C30 dialkyl amino; or C1~C30 alkoxy, $R_2$ and $R_2'$, which may be identical or different, are each a hydrogen atom; hydroxy; halogen; C1~C6 linear or branched alkyl; C3~C10 cycloalkyl; C1~C6 linear or branched alkoxy; C2~C20 heterocycloalkyl containing N, O or S as a heteroatom; phenyl, unsubstituted or substituted with at least one selected from the group consisting of a halogen atom, amino, nitryl, nitro, C1~C30 alkyl, C2~C30 alkenyl, C1~C30 alkoxy, C3~C30 cycloalkyl, C3~C30 heterocycloalkyl containing N, O or S as a heteroatom, C6~C30 aryl, and C5~C30 heteroaryl containing N, O or S as a heteroatom; N-acetyl-4'-piperidyl; N-propyl-4'-piperidyl; or $-(CH_2)_m X$ wherein m is an integer of 0 to 20, X is C2~C30 alkylester, C1~C30 alkylamide, C2~C30 alkylether, or carboxylic acid; or $R_2$ and $R_2'$ may form a ring, together, R3 is a hydrogen atom; C1~C6 linear or branched alkyl; C3~C10 cycloalkyl; C1~C6 linear or branched alkoxy; phenyl, unsubstituted or substituted with at least one selected from the group consisting of a halogen atom, amino, nitryl, nitro, C1~C30 alkyl, C2~C30 alkenyl, C1~C30 alkoxy, C3~C30 cycloalkyl, C3~C30 heterocycloalkyl containing N, O or S as a heteroatom, C6~C30 aryl, and C5~C30 heteroaryl containing N, O or S as a heteroatom; C2~C20 heterocycloalkyl containing N, O or S as a heteroatom; benzyl, unsubstituted or substituted with at least one selected from the group consisting of a halogen atom, amino, nitryl, nitro, C1~C30 alkyl, C2~C30 alkenyl, C1~C30 alkoxy, C3~30 cycloalkyl, C3~C30 heterocycloalkyl containing N, O or S as a heteroatom, C6~C30 aryl, and C5~C30 heteroaryl containing N, O or S as a heteroatom; p-methylphenyl, m-methylphenyl, o-methylphenyl; p-tert-butylethylphenyl, m-tert-butylethylphenyl, or o-tert-butylethylphenyl; p-methoxyphenyl, m-methoxyphenyl, or o-methoxyphenyl; p-fluorophenyl, m-fluorophenyl, or o-fluorophenyl; p-iodophenyl, m-iodophenyl, or o-iodophenyl; p-nitrophenyl, m-nitrophenyl, or o-nitrophenyl; p-chlorophenyl; m-chlorophenyl, or o-chlorophenyl; or p-bromophenyl, m-bromophenyl, or o-bromophenyl.

2. The method of treating inflammation of claim 1, wherein R1 is a hydrogen atom or hydroxy; $R_2$ and $R_2'$, which may be identical or different, are each independently methyl or cyclophetyl; and R3 is phenyl or p-methylphenyl.

3. The method of treating inflammation of claim 1, wherein the compound represented by Chemical Formula 1 is at least one selected from the group consisting of compounds represented by the following Chemical Formulas 2 to 51:

[Chemical Formula 2]
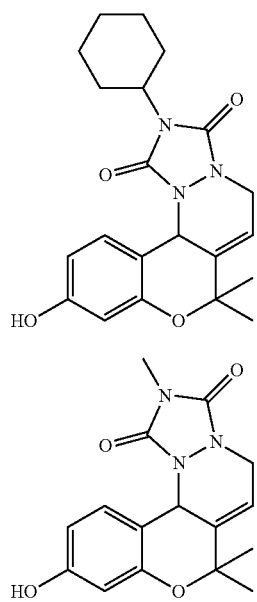
[Chemical Formula 3]
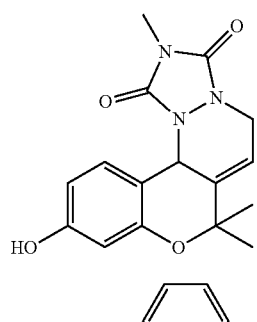
[Chemical Formula 4]
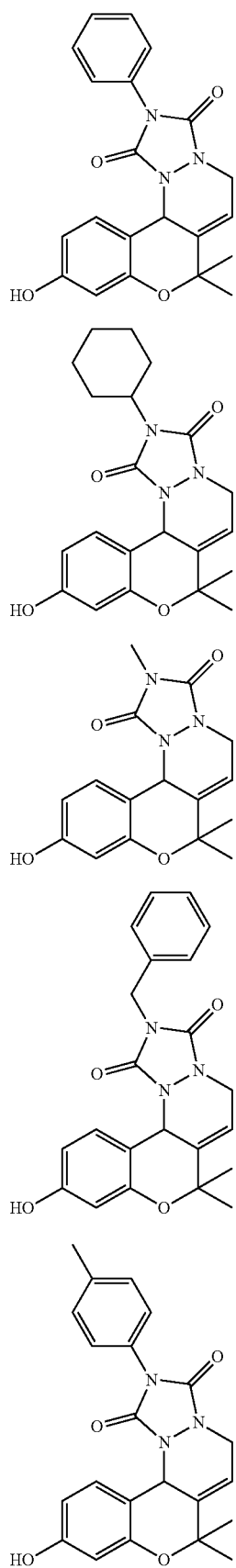
[Chemical Formula 5]
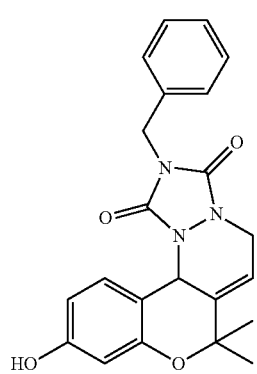
[Chemical Formula 6]
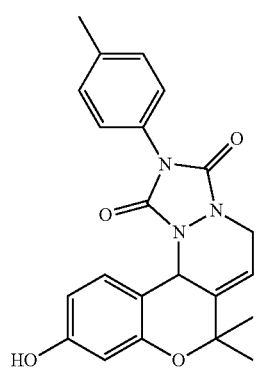
-continued
[Chemical Formula 7]
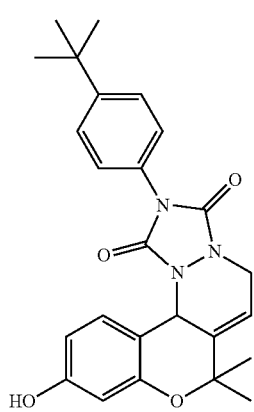
[Chemical Formula 8]
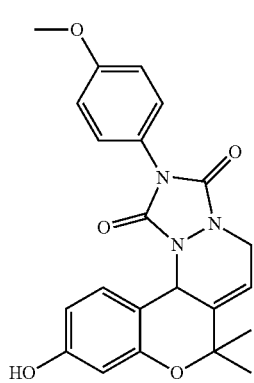
[Chemical Formula 9]
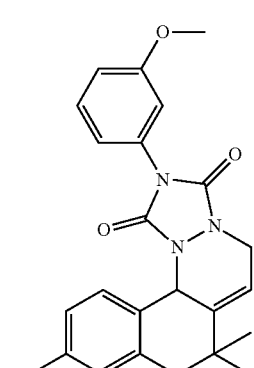
[Chemical Formula 10]
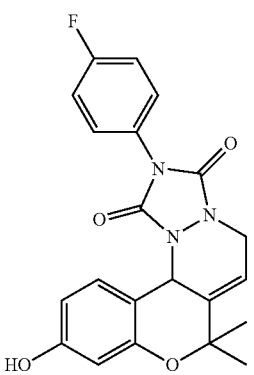

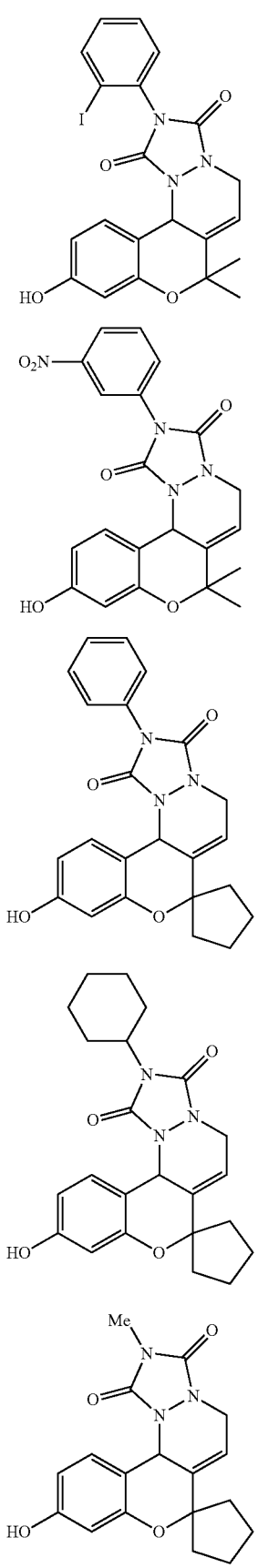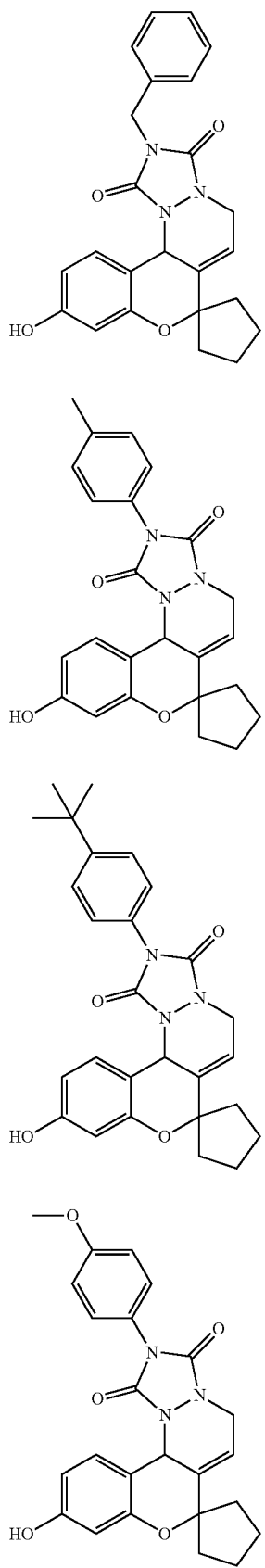

[Chemical Formula 20]
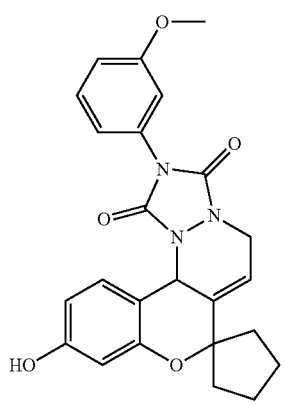
[Chemical Formula 21]
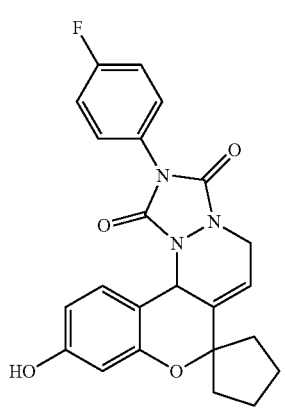
[Chemical Formula 22]
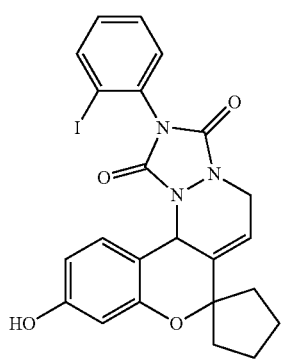
[Chemical Formula 23]
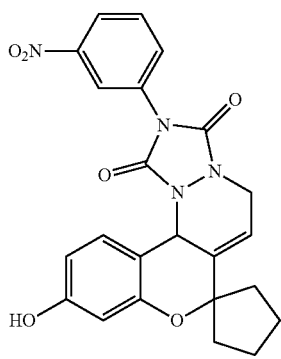
[Chemical Formula 24]
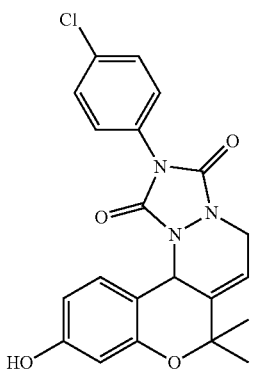
[Chemical Formula 25]
[Chemical Formula 26]
[Chemical Formula 27]
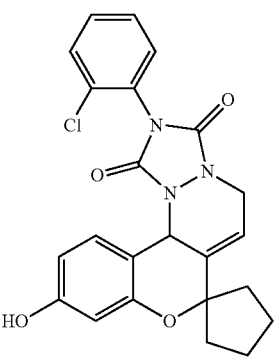

-continued
[Chemical Formula 28]
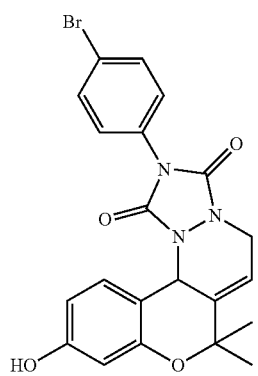
[Chemical Formula 29]
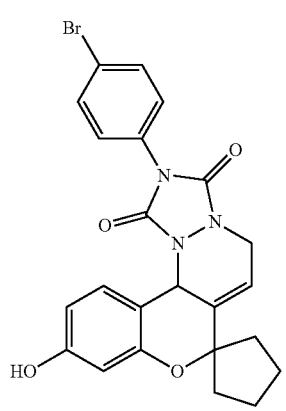
[Chemical Formula 30]
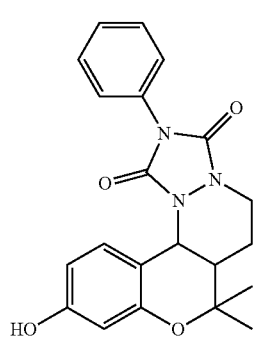
[Chemical Formula 31]
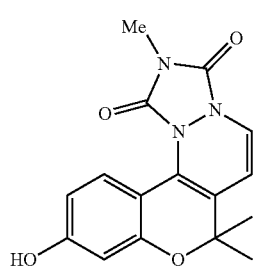
-continued
[Chemical Formula 32]
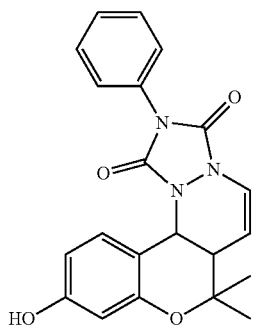
[Chemical Formula 33]
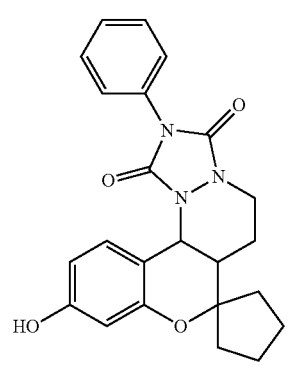
[Chemical Formula 34]
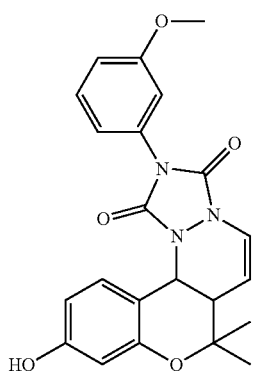
[Chemical Formula 35]
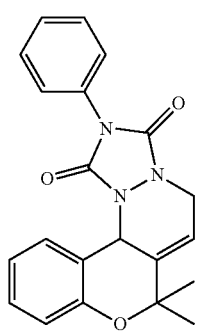

[Chemical Formula 36]
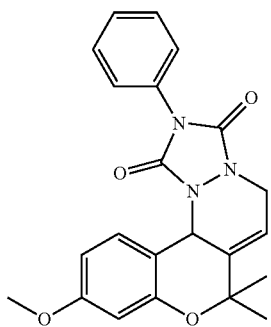
[Chemical Formula 37]
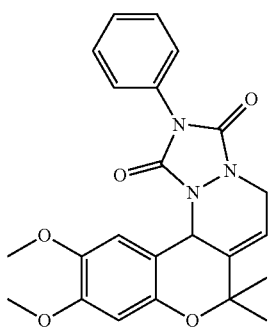
[Chemical Formula 38]
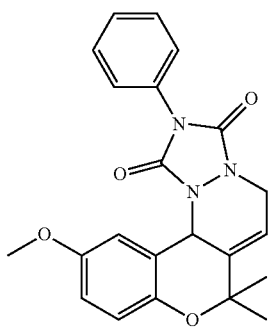
[Chemical Formula 39]
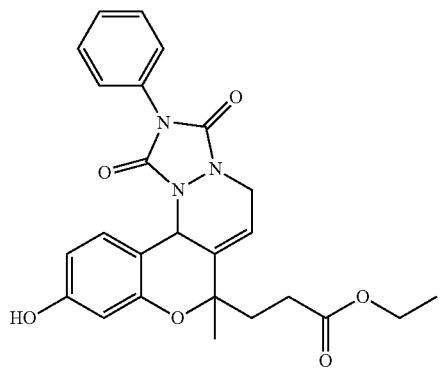
[Chemical Formula 40]
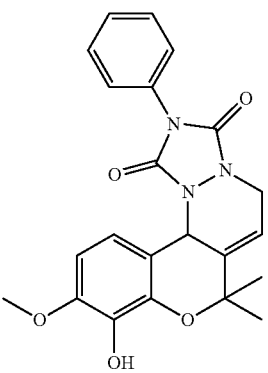
[Chemical Formula 41]
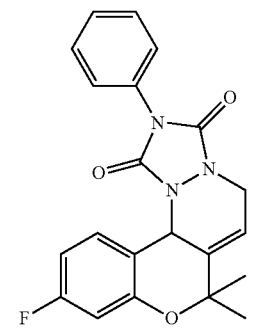
[Chemical Formula 42]
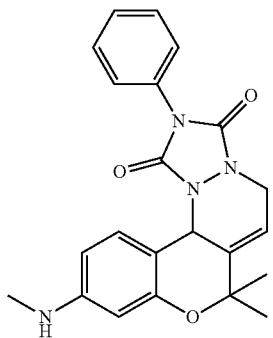
[Chemical Formula 43]
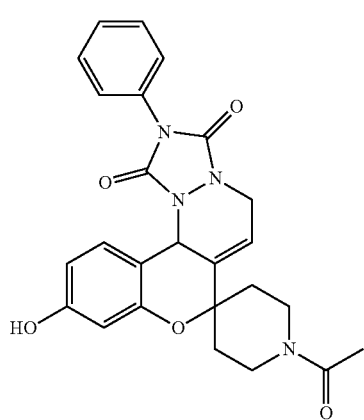

[Chemical Formula 44]
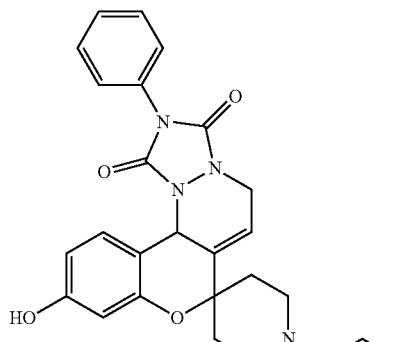
[Chemical Formula 45]
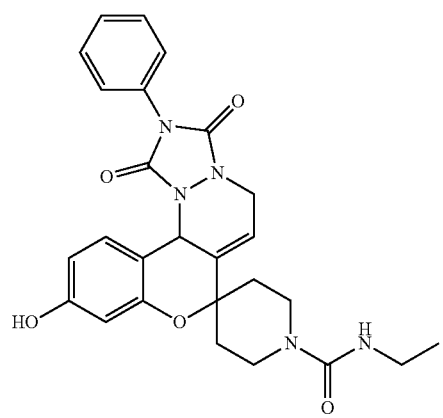
[Chemical Formula 46]
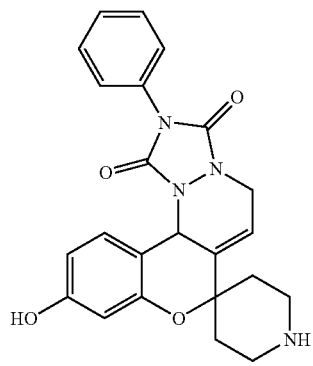
[Chemical Formula 47]
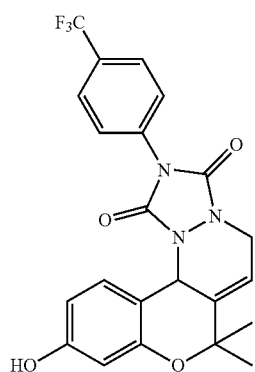
[Chemical Formula 48]
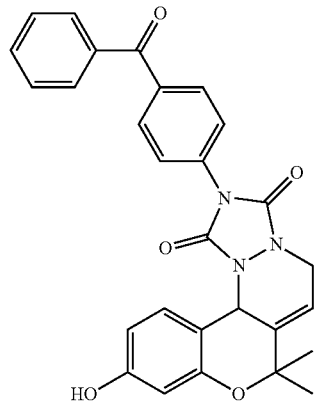
[Chemical Formula 49]
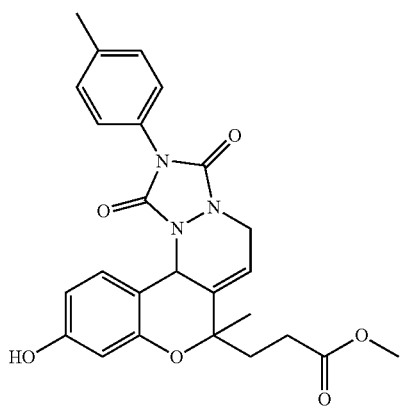
[Chemical Formula 50]
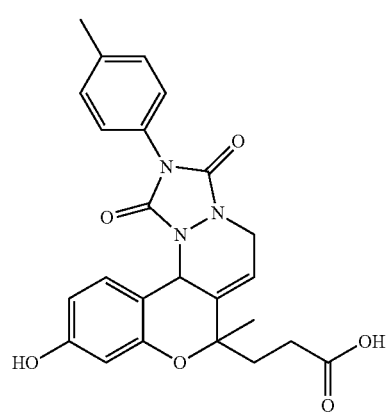

[Chemical Formula 51]

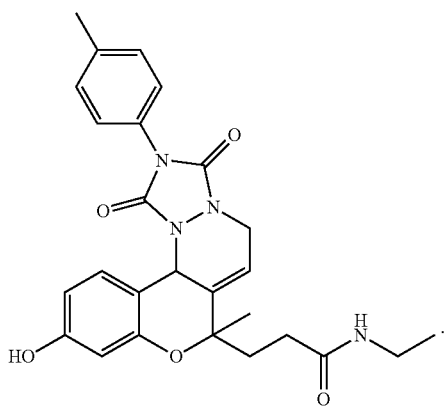

4. The method of treating inflammation of claim 1, wherein the inflammation is associated with at least one disease selected from the group consisting of gastritis, colitis, rheumatoid arthritis, nephritis, hepatitis, pancreatitis, sepsis, seizure, multiple sclerosis, Alzheimer's disease, Parkinson's disease, Huntington's disease, amyotrophic lateral sclerosis (Lou Gehrig's disease), stroke, trauma, spinal cord injury, and cancer.

5. The method of treating inflammation of claim 1, wherein the pharmaceutical composition suppresses inflammation by perturbing the post-translational modification of HMGB proteins.

6. The method of treating inflammation of claim 1, wherein the pharmaceutical composition further comprises a pharmaceutically acceptable drug, carrier or excipient.

\* \* \* \* \*